US011033536B2

(12) United States Patent
Borody

(10) Patent No.: US 11,033,536 B2
(45) Date of Patent: Jun. 15, 2021

(54) COMPOSITIONS AND METHODS FOR TREATING, AMELIORATING AND PREVENTING *H. PYLORI* INFECTIONS

(71) Applicant: CENTRE FOR DIGESTIVE DISEASES, Five Dock (AU)

(72) Inventor: Thomas Julius Borody, Five Dock (AU)

(73) Assignee: CENTRE FOR DIGESTIVE DIEASES, Five Dock (AU)

( * ) Notice: Subject to any disclaimer, the term of this patent is extended or adjusted under 35 U.S.C. 154(b) by 0 days.

(21) Appl. No.: 16/451,781

(22) Filed: Jun. 25, 2019

(65) Prior Publication Data
US 2019/0314355 A1 Oct. 17, 2019

Related U.S. Application Data

(63) Continuation of application No. PCT/AU2018/000195, filed on Oct. 15, 2018.

(60) Provisional application No. 62/572,512, filed on Oct. 15, 2017.

(51) Int. Cl.
| A61K 31/44 | (2006.01) |
| A61K 31/43 | (2006.01) |
| A61K 31/33 | (2006.01) |
| A61K 31/4439 | (2006.01) |
| A61P 31/04 | (2006.01) |
| A61K 31/4178 | (2006.01) |
| A61K 31/424 | (2006.01) |
| A61K 31/426 | (2006.01) |
| A61K 31/438 | (2006.01) |
| A61K 31/5383 | (2006.01) |
| A61K 31/65 | (2006.01) |
| A61K 33/245 | (2019.01) |

(52) U.S. Cl.
CPC ...... *A61K 31/4439* (2013.01); *A61K 31/4178* (2013.01); *A61K 31/424* (2013.01); *A61K 31/426* (2013.01); *A61K 31/43* (2013.01); *A61K 31/438* (2013.01); *A61K 31/5383* (2013.01); *A61K 31/65* (2013.01); *A61K 33/245* (2013.01); *A61P 31/04* (2018.01)

(58) Field of Classification Search
CPC .......................... A61K 31/4439; A61K 31/43
USPC ....................... 514/343, 183, 198
See application file for complete search history.

(56) References Cited

U.S. PATENT DOCUMENTS

| 6,132,768 A * | 10/2000 | Sachs | A61K 31/495 |
| | | | 424/457 |
| 2008/0139639 A1* | 6/2008 | Kajino | A61K 31/4025 |
| | | | 514/423 |
| 2009/0060983 A1* | 3/2009 | Bunick | A61K 9/0056 |
| | | | 424/440 |
| 2015/0110838 A1* | 4/2015 | Agrawal | A61K 39/3955 |
| | | | 424/400 |

FOREIGN PATENT DOCUMENTS

| CN | 104814964 A | 8/2015 |
| EP | 2710901 A1 * | 3/2014 ........... A23L 33/135 |

OTHER PUBLICATIONS

Martinucci et al. "Vonoprazan fumarate for the management of acid related diseases," Expert Opinion on Pharmacotherapy, Jul. 2017, vol. 18, No. 11, 1145-1152. (Year: 2017).*
Cammarota et al. ("Review article: biofilm formation by Helicobacter pylori as a target for eradication of resistant infection," Aliment Pharmaceutical Ther. 2012, vol. 36, pp. 222-230. (Year: 2012).*
Nseir et al. "Randomised clinical trial: simvastatin as adjuvant therapy improves significantly the Helicobacter pylori eradication rate-a placebo-controlled study," Alimentary Pharmacology and Therapeutics, 2012, vol. 36, pp. 231-238. (Year: 2012).*
Liu et al. ("Efficacy and pharmacological mechanism of pronase-enhanced low-dose antibiotics for Helicobacter pylori eradication," Antimicrobial Agents and Chemotherapy, 2014, vol. 58, No. 6, pp. 3348-3353). (Year: 2014).*
Ojetti et al. "Beta-lactamase inhibitor enhance helicobacter pylori eradication rate," J. Internal Medicine, 2004, vol. 255, pp. 125-129 (Year: 2004).*
Sugano, "Vonoprazan fumarate, a novel potassiumcompetitive acid blocker, in the management of gastroesophageal reflux disease: safety and clinical evidence to date" Therapeutic Advances in Gastroenterology, 2018, v 11, p. 1-14.
Sue et al., "First-Line Helicobacter pylori Eradication with Vonoprazan, Clarithromycin, and Metronidazole in Patients Allergic to Penicillin" Gastroenterology Research and Practice, v 2017, 6 pages.
Shinozaki et al., "Pre-treatment with proton pump inhibitors decreases the success of primary Helicobacter pylori eradication using a vonoprazan-based regimen" Kaohsiung Journal of Medical Sciences, 2018, v 34, p. 456-460.
Shinozaki et al., "Comparison of vonoprazan and proton pump inhibitors for eradication of Helicobacter pylori" Kaohsiung Journal of Medical Sciences, 2016, v 32, p. 255-260.

(Continued)

*Primary Examiner* — Shengjun Wang
(74) *Attorney, Agent, or Firm* — Greer, Burns & Crain, Ltd.; Gregory P. Einhorn

(57) ABSTRACT

Provided are methods for treating, ameliorating, reversing and/or preventing a *Helicobacter pylori* (*H. pylori*) infection in an individual in need thereof, comprising: administering to the individual in need thereof a therapeutic combination comprising: (a) a composition comprising or consisting of: vonoprazan or a vonoprazan fumarate, or a 5-(2-fluorophenyl)-1-(pyridin-3-ylsulfonyl)-1H-pyrrol-3-yl)-N-methyl-methanamine monofumarate, or a 1-(5-(2-fluorophenyl)-1-(pyridin-3-ylsulfonyl)-1H-pyrrol-3-yl)-N-methyl-methanamine fumarate), optionally TAKECAB™; and (b) an antimicrobial or antibiotic drug or composition.

28 Claims, No Drawings

(56) References Cited

OTHER PUBLICATIONS

Sakurai et al., "Comparative study: Vonoprazan and proton pump inhibitors in Helicobacter pylori eradication therapy" World J Gastroenterol, Jan. 28, 2017, v 23, n 4, p. 668-675.

Saito et al., "Vonoprazan-Based Third-Line Therapy Has a Higher Eradication Rate against Sitafloxacin-Resistant Helicobacter pylon" Cancers, 2019, v 11, n 116, p. 1-8.

Ohtaka et al., "Efficacy and Tolerability of Second-Line Metronidazole Triple Therapy Using Vonoprazan for Helicobacter pylon Eradication in Japan—Comparative Study: Vonoprazan vs. Proton Pump Inhibitors" Open Journal of Gastroenterology, 2018, v 8, p. 27-38.

Murakami et al., "Vonoprazan, a novel potassium-competitive acid blocker, as a component of first-line and second-line triple therapy for Helicobacter pylon eradication: a phase III, randomised, double-blind study" Gut, 2016, v 65, p. 1439-1446.

Lyu et al., "Efficacy and Safety of Vonoprazan-Based versus Proton Pump Inhibitor-Based Triple Therapy for Helicobacter pylon Eradication: A Meta-Analysis of Randomized Clinical Trials" BioMed Research International, v 2019, 8 pages.

Kusunoki et al., "Effect of Age on Effectiveness of Vonoprazan in Triple Therapy for Helicobacter pylori Eradication" Intern Med Advance Publication, 2018, p. 1-8.

Abadi et al., "Vonoprazan and Helicobacter pylon Treatment: A Lesson From Japan or a Limited Geographic Phenomenon?" Frontiers in Pharmacology, Apr. 2019, v 10, Article 316, p. 1-6.

Kim et al., "Vonoprazan-Based Helicobacter pylori Eradication Therapy: Time to Get Kompetitive?" Dig Dis Sci, 2017, v 62, p. 2955-2957.

Kinoshita et al., "Evaluation of the Efficacy and Safety of Vonoprazan in Patients with Nonerosive Gastroesophageal Reflux Disease:A Phase III,Randomized, Double-Blind, Placebo-Controlled, Multi-center Study" Current TherapeuticResearch, 2016, p. 1-7.

Akazawa et al., "Vonoprazan-based therapy for Helicobacter pylori eradication: experience and clinical evidence" Therapeutic Advances in Gastroenterology, 2016, v 9, n 6, p. 845-852.

Graham et al., "Update on the Use of Vonoprazan: A Competitive Acid Blocker" Gastroenterology, 2018, v 154, p. 462-466.

Miyamoto et al., "Parietal Cell Protrusions and Dilated Oxyntic Glands from Use of Vonoprazan" The American Journal of Gastroenterology, 207, v 112, p. 1899-1901, 2017.

Jung et al., "Systematic review with meta-analysis: the efficacy of vonoprazan-based triple therapy on Helicobacter pylori eradication" Aliment Pharmacol Ther., v 46, p. 106-114, 2017.

Nagata et al., "Successful eradication of Helicobacter pylori with a herbal medicine, goshuyuto (Wu Zhu Yu Tang), plus rabeprazole after failure of triplet therapy with vonoprazan: a report of three cases" Department of Oriental Traditional Medical Center, 13 pages, 2019.

Murakami et al., "In a world of increasing resistance emerges a hope to eradicate Helicobacter pylori: Vonoprazan" Turk J Gastroenterol, 2016, v 27, p. 296-297.

Molina-Infante et al., "Latest advances in the treatment of Helicobacter pylori infection" Acta Gastroenterol Latinoam, 2017, v 47, n 1, p. 75-85.

Nishizawa et al, "Effects of patient age and choice of antisecretory agent on success of eradication therapy for Heliobacter pylori infection" J. Clin. Biochem. Nutr, May 2017, v 60, n 3, p. 208-210.

Graham et al., "Helicobacter pylori therapy: a paradigm shift" Expert Review of Anti-Infective Therapy, 2016, v 14, n 6, p. 577-585.

Baryshnikova et al., "Eradication of Helicobacter Pylori Infection: Past, Present, and Future" J Clin Gastroenterol Treat, 2016, v 2, Issue 1, p. 1-10.

Anzai et al., "Improvement of Dissolution Properties of a New Helicobacter pylori Eradicating Agent (TG44) by Inclusion Complexation with beta-Cyclodextrin" Chem. Pharm. Bull., 2007, v 55, n 10, p. 1466-1470.

Abd-Elsalam et al., "A 2-week Nitazoxanide-based quadruple treatment as a rescue therapy for Helicobacter pylori eradication" Medicine, 2016, v 85 , n 24, p. 1-4.

International Search Report and for Written Opinion PCT/AU2018/000195, dated Dec. 19, 2018.

Nickitas-Etienne, International Preliminary Report on Patentability for PCT/AU2018/000195, dated Apr. 21, 2020.

* cited by examiner

COMPOSITIONS AND METHODS FOR TREATING, AMELIORATING AND PREVENTING *H. PYLORI* INFECTIONS

RELATED APPLICATIONS

This application is a continuation application claiming benefit of priority to Patent Cooperation Treaty (PCT) International Application Serial No: PCT/AU2018/000195, filed Oct. 15, 2018, which claims benefit of priority to U.S. Provisional Patent Application Ser. No. ("USSN") 62/572, 512, filed Oct. 15, 2017. The aforementioned applications are expressly incorporated herein by reference in their entirety and for all purposes.

TECHNICAL FIELD

This invention generally relates to infectious diseases and medicine. In alternative embodiments, provided are therapeutic combinations, including products of manufacture and kits, and methods, for treating, ameliorating, reversing and/or preventing (acting as a prophylaxis) a *Helicobacter pylori* (*H. pylori*) infection in an individual in need thereof.

BACKGROUND

The history of *Helicobacter pylori* (*H. pylori*) eradication dates back to 1984 when the first triple therapy was developed in Australia by Borody at the Centre for Digestive Diseases. It consisted of Bismuth, Tetracycline, and Flagyl. Its long term effects were reported in 1989 and it was dispensed to patients as a separately-prescribed combination written on prescriptions by most physicians until the commercial product called Helidac was placed on the market in several countries. Since that time numerous Triple Therapies have been described with the one most utilised being a combination consisting of a Proton Pump Inhibitor (PPI), amoxicillin and clarithromycin. However, there has been a progressive fall in the efficacy of this combination due to *H. pylori* developing resistance to clarithromycin and hence, alternate therapies are being sought.

In Japan a new acid suppressant called vonoprazan or vonoprazan fumarate [5-(2-fluorophenyl)-1-(pyridin-3-ylsulfonyl)-1H-pyrrol-3-yl)-N-methylmethanamine monofumarate], also sold as TAKECAB™ (CAS#: 1260141-27-2,1-(5-(2-fluorophenyl)-1-(pyridin-3-ylsulfonyl)-1H-pyrrol-3-yl)-N-methylmethanamine fumarate), which is a potassium-competitive acid blocker has been approved. It causes prolonged and profound inhibition of gastric acid secretion and has gained clinical acceptance in treating erosive oesophagitis and peptic ulcers. An unusual, but useful advantage of vonoprazan over a Proton Pump Inhibitor (PPI) in the amoxicillin and clarithromycin combination is that the efficacy increases quite markedly. This is without any added adverse events nor any more than observed with the standard triple therapies with conventional Proton Pump Inhibitors (PPIs).

The chemical advantage of vonoprazan is that it does not require acid for activation. It is rapidly absorbed in the intestine and leads to fast inhibition of acid secretion. It is more stable at neutral pH compared with conventional PPI's and has plasma half-life of 7 hours after a single 20 mg ingestion. This is longer than the conventional PPI's which have a half-life less than 2 hours permitting the gastric pH to fall back into acidic range. It is not metabolised through the hepatic CYP2C19 haplotypes, but rather by the CYP3A4 system. For this reason, vonoprazan exerts rapid, strong, prolonged and stable inhibition of $H^+/K^+$—ATPAs (ATP synthase subunit alpha). Vonoprazan manages to increase intragastric pH to at least over pH 4.0 within 4 hours of its first administration in humans creating conditions within which the antibiotics amoxicillin and clarithromycin are stable in conjunction.

As a result of vonoprazan's pH elevating activity when compared it has been observed that the *H. pylori* (HP) eradication rate with vonoprazan, amoxicillin and clarithromycin has frequently resulted in 93% eradication with versus (vs.) 76% eradication with lansoprazole (PPI) as first line therapy. Other studies have showed similar wide efficacy differences with vonoprazan vs PPI combinations, many of them over 92%. Most have ranged between 88% and 94% as first line therapy. Vonoprazan has been used as 'Second Line Therapy' using metronidazole, amoxicillin, and vonoprazan twice daily for 7 days reaching an eradication rate of close to 100%. The vonoprazan, amoxicillin and clarithromycin still has a fairly high eradication rate in the low 80's. It is the enhanced activity of the amoxicillin (although not as effective as when containing an added clarithromycin) which makes the eradication so powerful to the extent that dual therapy with amoxicillin and vonoprazan has been proposed as a potential 'First Line' therapy.

While these therapies have achieved some degree of success, a significant number of treatments still remain failures (see e.g., Akazawa Y et al. 2016, Therap Adv Gastroenterol, 9:845) which can result in adverse effects in the non-responding patients and antibiotic resistance in non-responders. To be clinically effective or useful, *H. pylori* (HP) eradication efficacy of a therapeutic regimen should reach close to or over 90%—otherwise it is not sufficiently clinically effective. The existing amoxicillin and clarithromycin PPI protocols were initially able to achieve greater than 85% eradication and became the "standard of care protocols" in many parts of the world. However, the rising resistance to clarithromycin has brought an end to the clinical usefulness of this combination in numerous regions of the world. Some eradication rates have fallen from 90% down to less than 50%.

SUMMARY

In alternative embodiments, provided are methods for treating, ameliorating, reversing and/or preventing (acting as a prophylaxis) a *Helicobacter pylori* (*H. pylori*) infection in an individual in need thereof, comprising:
administering to the individual in need thereof a therapeutic combination comprising:
(a) a composition comprising or consisting of: vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methylmethanamine fumarate), optionally TAKECAB™; and
(b) an antimicrobial or antibiotic drug or composition comprising or consisting of:
(i)
(1) an amoxicillin, administered to the individual in need thereof at a dose of between about 1 gram (g) to about 2 g twice daily (bid), and optionally the amoxicillin is formulated as amoxicillin/clavulanic acid, also known as co-amoxiclav, or is optionally ACTIMOXI™, ALPHAMOX™, AMOCLA™, TYCIL™, AMOXIL™, TRIMOX™; and
(2) a clarithromycin, optionally BIAXIN™, administered to the individual in need thereof at a dose of between about 100 mg to about 2 g twice daily, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 20 mg to about 50 mg twice daily (bid), or for about 25 mg or more twice daily (bid);

(ii)
(1) an amoxicillin, administered to the individual in need thereof at a dose of between about 500 gm to about 1 g three times daily (tid), and optionally the amoxicillin is formulated as amoxicillin/clavulanic acid, also known as co-amoxiclav, or is optionally ACTIMOXI™, ALPHAMOX™, AMOCLA™, TYCIL™, AMOXIL™, TRIMOX™; and
(2) a metronidazole, optionally FLAGYL™, METRO™, administered to the individual in need thereof at a dose of between about 200 mg to about 500 mg three times daily (tid),
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 20 mg to about 50 mg three times daily (tid), or for about 25 mg or more three times daily (tid);

(iii)
(1) an amoxicillin, administered to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a rifabutin, optionally MYCOBUTIN™, administered to the individual in need thereof at a dose of between about 50 mg to about 250 mg twice daily (bid) or three times daily (tid),
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(iv)
(1) an amoxicillin, administered to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a levofloxacin, administered to the individual in need thereof at a dose of between about 100 mg to about 500 mg twice daily (bid) or three times daily (tid), wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(v)
(1) an amoxicillin, administered to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a ciprofloxacin, optionally CILOXAN™, CIPRO™, NEOFLOXIN™ administered to the individual in need thereof at a dose of between about 100 mg to about 500 mg twice daily (bid) or three times daily (tid),
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(vi)
(1) an amoxicillin, administered to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a moxifloxacin, optionally AVELOX™, VIGAMOX™, MOXEZA™, administered to the individual in need thereof at a dose of between about 25 mg to about 500 mg per day,
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(vii)
(1) an amoxicillin, a clarithromycin, a metronidazole, a levofloxacin, a ciprofloxacin or a moxifloxacin, administered to the individual in need thereof at a dose as set forth in any of steps (i) to (vi), and optionally the amoxicillin is formulated as amoxicillin/clavulanic acid, also known as co-amoxiclav, or is optionally ACTIMOXI™, ALPHAMOX™, AMOCLA™, TYCIL™, AMOXIL™, TRIMOX™; and
(2) a TG44, or a 1-1000 mg/d] {[4-methylbenzyl 4'-[trans-4-(guanidine-methyl) cyclohexyl carbonyloxy] biphenyl-4-carboxylate monohydrochloride}, or CAS registry number 178748-55-5, administered to the individual in need thereof at a dose of between about 15 mg to about 50 mg per day, or at about 50 to 500 mg per day, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 50 mg, or 20 mg or more, twice daily (bid) or three times daily (tid);

(viii)
(1) an amoxicillin,
(2) a furazolidone, optionally FUROXONE™, DEPENDAL-M™, administered to the individual in need thereof at a dose of between about 50 to about 600 mg/d, and
(3) a rifabutin, optionally MYCOBUTIN™, administered to the individual in need thereof at a dose of between about 60 to about 450 mg/d, and optionally the rifabutin dose is ramped up starting at about 40 to about 60 g bid or tid, and optionally rising over 3 days to about 200 to about 450/d, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose as set forth in any of (i) to (vii);
(ix) a therapeutic combination as set forth in Table 1; or
(x) any combination of (i) to (ix).

In alternative embodiments there is provided a method for treating or preventing *Helicobacter pylori* (*H. pylori*) infection in an individual in need thereof, the method comprising administering to the individual in need thereof a therapeutic combination comprising:
(a) vonoprazan, and
(b) a prolonged release formulation of an antibiotic comprising:
(1) amoxicillin wherein optionally the amoxicillin is formulated as amoxicillin/clavulanic acid, and/or
(2) an antibiotic selected from the group consisting of clarithromycin, azithromycin, roxithromycin and erythromycin,
wherein the vonoprazan is administered in an amount of 10 mg to 1 g per day, and the amoxicillin is administered in an amount of 10 mg to 6 g per day.

In alternative embodiments there is provided a method for treating or preventing *Helicobacter pylori* (*H. pylori*) infection in an individual in need thereof, the method comprising administering to the individual in need thereof a therapeutic combination comprising:
(a) a prolonged release microencapsulated and/or multimatrix formulation of vonoprazan, and
(b) a prolonged release microencapsulated and/or multimatrix formulation of amoxicillin wherein optionally the amoxicillin is formulated as amoxicillin/clavulanic acid, or
(c) a prolonged release microencapsulated and/or multimatrix formulation of vonoprazan and amoxicillin wherein optionally the amoxicillin is formulated as amoxicillin/clavulanic acid,
wherein the vonoprazan is administered in an amount of 10 mg to 1 g per day, and the amoxicillin is administered in an amount of 1 g to 6 g per day.

In alternative embodiments there is provided a method for treating or preventing *Helicobacter pylori* (*H. pylori*) infection in an individual in need thereof, the method comprising administering to the individual in need thereof a therapeutic combination comprising:
(a) vonoprazan,
(b) a proton pump inhibitor, and
(c) at least one antibiotic selected from the group consisting of amoxicillin, wherein optionally the amoxicillin is formulated as amoxicillin/clavulanic acid, ampicillin, pivampicillin, hetacillin, bacampicillin, metampicillin, talampicillin, epicillin, a macrolide antibiotic, furazolidone, ciprofloxacin, levofloxacin, tetracycline, a nitroimidazole antibiotic, bismuth, an ansamycin antibiotic, and nitazoxanide, wherein optionally the proton pump inhibitor is selected from the group consisting of omeprazole; pantoprazole; esomeprazole, lansoprazole, and rabeprazole, wherein optionally the macrolide antibiotic is selected from the group consisting of azithromycin, clarithromycin, erythromycin, fidaxomicin, and telithromycin,
wherein optionally the nitroimidazole antibiotic is selected from the group consisting of metronidazole, tinidazole, and secnidazole,
wherein optionally the ansamycin antibiotic is selected from the group consisting of rifabutin, rifampicin, rifapentin, and rifamixin.

In alternative embodiments there is provided a method for treating or preventing *Helicobacter pylori* (*H. pylori*) infection in an individual in need thereof, the method comprising administering to the individual in need thereof a therapeutic combination comprising
(i) amoxicillin, vonoprazan, furazolidone, and rifabutin;
(ii) amoxicillin, vonoprazan, bismuth, furazolidone, rifabutin;
(iii) amoxicillin, vonoprazan, bismuth, levofloxacin, rifabutin;
(iv) amoxicillin, vonoprazan, levofloxacin, rifabutin;
(v) amoxicillin, vonoprazan, bismuth, levofloxacin, furazolidone, rifabutin;
(v) amoxicillin, vonoprazan, bismuth, tetracycline, rifabutin;
(vi) metronidazole, vonoprazan, bismuth, tetracycline, rifabutin;
(v) vonoprazan, bismuth, levofloxacin, rifabutin; or
(vi) amoxicillin, vonoprazan, furazolidone, rifabutin, bismuth, and nitazoxanide,
wherein optionally the amoxicillin is formulated as amoxicillin/clavulanic acid.

In alternative embodiments of methods as provided herein: the therapeutic combination is administered to the individual in need thereof for about 2, 3, 4, 5, 6, 7, 8, 9, 10, 11, 12, 13 or 14 or more days; or the therapeutic combination is, is contained in or comprises a formulation, a pharmaceutical preparation or a pharmaceutical composition.

In alternative embodiments of methods as provided herein: the vonoprazan or vonoprazan fumarate, or the 5-(2-fluorophenyl)-1-(pyridin-3-ylsulfonyl)-1H-pyrrol-3-yl)-N-methylmethanamine monofumarate, or the 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof:
(a) at a unit dosage of between about 5 mg to about 200 mg per day, or
(b) in a unit dosage form of between about 10 mg and 200 mgm, or between about between about 40 mg and 100 mgm, or is about 10, 20, 30, 40, 50, 60, 70, 75, 80, 90 or 100 mg per unit dose,
which optionally can be administered once a day, bid or tid, or a four times a day, five times a day or six times a day or more, regimen.

In alternative embodiments of methods as provided herein: the therapeutic combination, or the formulation, the pharmaceutical or the pharmaceutical preparation, is formulated as a chewable delivery vehicle, a gum, a gummy, a candy, a lozenge, an ice cream or an ice, or a yogurt.

In alternative embodiments of methods as provided herein: the therapeutic combination, or the formulation, the pharmaceutical or the pharmaceutical preparation, further comprises a flavoring or a sweetening agent, an aspartamine, a stevia, monk fruit, a sucralose, a saccharin, a cyclamate, a xylitol, a vanilla, an artificial vanilla or chocolate or strawberry flavor, an artificial chocolate essence, or a mixture or combination thereof.

In alternative embodiments of methods as provided herein: the therapeutic combination, or the formulation, the pharmaceutical or the pharmaceutical preparation, further comprises a preservative, a benzoic acid or a potassium sorbate.

In alternative embodiments of methods as provided herein: the therapeutic combination, or the formulation, the pharmaceutical or the pharmaceutical preparation, further comprises, or has added to: at least one probiotic or prebiotic, wherein optionally the prebiotic comprises an inulin, lactulose, extracts of artichoke, chicory root, oats, barley, various legumes, garlic, kale, beans, flax or an herb, wherein optionally the probiotic comprises a cultured or stool-extracted microorganism or bacteria, or a bacterial component, and optionally the bacteria or bacterial component comprises or is derived from a *Saccharomyces boulardii, Bacteroidetes*, a *Firmicutes*, a *Lactobacilli*, a *Bifidobacteria*, an *E coli*, a *Strep fecalis* and equivalents.

In alternative embodiments of methods as provided herein: the therapeutic combination, or the formulation, the pharmaceutical or the pharmaceutical preparation, further comprises, or has added to: at least one congealing agent, wherein optionally the congealing agent comprises an arrowroot or a plant starch, a powdered flour, a powdered potato or potato starch, an absorbant polymer, an Absorbable Modified Polymer, and/or a corn flour or a corn starch.

In alternative embodiments of methods as provided herein: the therapeutic combination, or the formulation, the pharmaceutical or the pharmaceutical preparation, further comprises an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient.

In alternative embodiments of methods as provided herein: the therapeutic combination, or the formulation, the pharmaceutical or the pharmaceutical preparation, further comprises, or has added to: at least one Biofilm Disrupting Compound, wherein optionally the biofilm disrupting compound comprises an enzyme, a deoxyribonuclease (DNase), N-acetylcysteine, an auranofin, an alginate lyase, glycoside hydrolase dispersin B; a Quorum-sensing inhibitor, a ribonucleic acid III inhibiting peptide, *Salvadora persica* extracts, Competence-stimulating peptide, Patulin and penicillic acid; peptides—cathelicidin-derived peptides, small lytic peptide, PTP-7, Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, *Delisea* furanones, N-sulfonyl homoserine lactones or any combination thereof.

In alternative embodiments, the therapeutic combination, or the formulation, the pharmaceutical or the pharmaceutical preparation, further comprises, or has added to a statin selected from the group consisting of atorvastatin, fluvastatin, lovastatin, pitavastatin, pravastatin, rosuvastatin, and simvastatin.

In alternative embodiments the therapeutic combination, or the formulation, the pharmaceutical or the pharmaceutical preparation, further comprises, or has added to a pronase. Pronase refers to a mixture of several nonspecific endo- and exoproteases that digest proteins down to single amino acids.

In alternative embodiments of methods as provided herein: the therapeutic combination, or the formulation, the pharmaceutical or the pharmaceutical preparation, is formulated as a delayed or gradual enteric release composition or formulation, and optionally the formulation comprises a gastro-resistant coating designed to dissolve at a pH of 7 in the terminal ileum, e.g., an active ingredient is coated with an acrylic based resin or equivalent, e.g., a poly(meth)acrylate, e.g. a methacrylic acid copolymer B, NF, which dissolves at pH 7 or greater, e.g., comprises a multimatrix (MMX) formulation. Also provided is the therapeutic combination or composition of the invention formulated as a microencapsulated product, wherein a proportion of the combination or composition is released in stomach with an appropriate 'exploder' excipient and a proportion of the combination or composition is formulated in a MMX formulation, so as to deliver the combination or composition to the stomach immediately as well as to the small bowel for re-secretion into to stomach where the *H. pylori* resides.

In alternative embodiments of methods as provided herein: the therapeutic combination, or the formulation, the pharmaceutical or the pharmaceutical preparation, is contained in a delivery vehicle, product of manufacture, container, syringe, device or bag.

In alternative embodiments of methods as provided herein: the therapeutic combination, or the formulation, the pharmaceutical or the pharmaceutical preparation, is initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation.

In alternative embodiments, provided are therapeutic combinations comprising:
(a) a composition comprising or consisting of: vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™; and
(b) an antimicrobial or antibiotic drug or composition comprising or consisting of:
(i)
(1) an amoxicillin, formulated for administration to the individual in need thereof at a dose of between about 1 gram (g) to about 2 g twice daily (bid), and optionally the amoxicillin is formulated as amoxicillin/clavulanic acid, also known as co-amoxiclav, or is optionally ACTIMOXI™, ALPHAMOX™, AMOCLA™, TYCIL™, AMOXIL™, TRIMOX™; and
(2) a clarithromycin, optionally BIAXIN™, formulated for administration to the individual in need thereof at a dose of between about 100 mg to about 2 g twice daily, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 20 mg to about 50 mg twice daily (bid), or for about 25 mg or more twice daily (bid);

(ii)
(1) an amoxicillin, formulated for administration to the individual in need thereof at a dose of between about 500 gm to about 1 g three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a metronidazole, optionally FLAGYL™, METRO™, formulated for administration to the individual in need thereof at a dose of between about 200 mg to about 500 mg three times daily (tid),
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 20 mg to about 50 mg three times daily (tid), or for about 25 mg or more three times daily (tid);

(iii)
(1) an amoxicillin, formulated for administration to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a rifabutin, optionally MYCOBUTIN™, formulated for administration to the individual in need thereof at a dose of between about 50 mg to about 250 mg twice daily (bid) or three times daily (tid),
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 5 mg to about 200 mg or more twice daily (bid) or three times daily (tid);

(iv)
(1) an amoxicillin, formulated for administration to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a levofloxacin, formulated for administration to the individual in need thereof at a dose of between about 100 mg to about 500 mg twice daily (bid) or three times daily (tid),
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 5 mg to about 200 mg or more twice daily (bid) or three times daily (tid);

(v)
(1) an amoxicillin, formulated for administration to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a ciprofloxacin, optionally CILOXAN™, CIPRO™, NEOFLOXIN™, formulated for administration to the individual in need thereof at a dose of between about 100 mg to about 500 mg twice daily (bid) or three times daily (tid),
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 5 mg to about 200 mg or more twice daily (bid) or three times daily (tid);

(vi)
(1) an amoxicillin, formulated for administration to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a moxifloxacin, optionally AVELOX™, VIGAMOX™, MOXEZA™, formulated for administration to the individual in need thereof at a dose of between about 25 mg to about 500 mg per day,
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 5 mg to about 200 mg or more twice daily (bid) or three times daily (tid);

(vii)
(1) an amoxicillin, a clarithromycin, a metronidazole, a levofloxacin, a ciprofloxacin or a moxifloxacin, formulated for administration to the individual in need thereof at a dose as set forth in any of steps (i) to (vi), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a TG44, or a 1-1000 mg/d] {[4-methylbenzyl 4'-[trans-4-(guanidine-methyl) cyclohexyl carbonyloxy] biphenyl -4-carboxylate monohydrochloride}, or CAS registry number 178748-55-5, formulated for administration to the individual in need thereof at a dose of between about 15 mg to about 50 mg per day, or at about 50 to 500 mg per day,
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 5 mg to about 50 mg, or 20 mg or more, twice daily (bid) or three times daily (tid);

(viii)
(1) an amoxicillin,
(2) a furazolidone, optionally FUROXONE™, DEPENDAL-M™, formulated for administration to the individual in need thereof at a dose of between about 50 to about 600 mg/d, and
(3) a rifabutin, optionally MYCOBUTIN™, formulated for administration to the individual in need thereof at a dose of between about 60 to about 450 mg/d, and optionally the rifabutin dose is ramped up starting at about 40 to about 60 g bid or tid, and optionally rising over 3 days to about 200 to about 450/d, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose as set forth in any of (i) to (vii);

(ix) a therapeutic combination as set forth in Table 1; or (x) any combination of (i) to (ix).

In alternative embodiments, provided are kits or products of manufacture comprising a therapeutic combination as provided herein.

In alternative embodiments, provided are uses of a therapeutic combination as provided herein, or a kit or product of manufacture as provided herein, in the manufacture of a medicament.

In alternative embodiments, provided are therapeutic combinations for use in treating, ameliorating, reversing and/or preventing (acting as a prophylaxis) a *Helicobacter pylori* (*H. pylori*) infection in an individual in need thereof, wherein the therapeutic combination comprises a therapeutic combination as provided herein.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

In a first aspect, forms of the invention described herein include the following:

1. A method for treating, ameliorating, reversing and/or preventing (acting as a prophylaxis) a *Helicobacter pylori* (*H. pylori*) infection in an individual in need thereof, comprising:

administering to the individual in need thereof a therapeutic combination comprising:

(a) a composition comprising or consisting of: vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™; and (b) an antimicrobial or antibiotic drug or composition comprising or consisting of:

(i)

(1) an amoxicillin, administered to the individual in need thereof at a dose of between about 1 gram (g) to about 2 g twice daily (bid), optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and (2) a clarithromycin, optionally BIAXIN™, administered to the individual in need thereof at a dose of between about 100 mg to about 2 g twice daily, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 20 mg to about 50 mg twice daily (bid), or for about 25 mg or more twice daily (bid);

(ii)

(1) an amoxicillin, administered to the individual in need thereof at a dose of between about 500 gm to about 1 g three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and (2) a metronidazole, optionally FLAGYL™, METRO™, administered to the individual in need thereof at a dose of between about 200 mg to about 500 mg three times daily (tid), wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 20 mg to about 50 mg three times daily (tid), or for about 25 mg or more three times daily (tid);

(iii)

(1) an amoxicillin, administered to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and (2) a rifabutin, optionally MYCOBUTIN™, administered to the individual in need thereof at a dose of between about 50 mg to about 250 mg twice daily (bid) or three times daily (tid), wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(iv)

(1) an amoxicillin, administered to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and (2) a levofloxacin, administered to the individual in need thereof at a dose of between about 100 mg to about 500 mg twice daily (bid) or three times daily (tid), wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(v)

(1) an amoxicillin, administered to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and (2) a ciprofloxacin, optionally CILOXAN™, CIPRO™, NEOFLOXIN™, administered to the individual in need thereof at a dose of between about 100 mg to about 500 mg twice daily (bid) or three times daily (tid), wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(vi)

(1) an amoxicillin, administered to the individual in need thereof at a dose of between about 250 gm to about 1 g twice daily (bid) or three times daily (tid), and optionally the amoxicillin is formulated as amoxicillin/clavulanic acid, also known as co-amoxiclav, or is optionally ACTIMOXI™, ALPHAMOX™, AMOCLA™, TYCIL™, AMOXIL™, TRIMOX™; and (2) a moxifloxacin, optionally AVELOX™, VIGAMOX™, MOXEZA™, administered to the individual in need thereof at a dose of between about 25 mg to about 500 mg per day, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(vii)

(1) an amoxicillin, a clarithromycin, a metronidazole, a levofloxacin, a ciprofloxacin or a moxifloxacin, administered to the individual in need thereof at a dose as set forth in any of steps (i) to (vi), optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and (2) a TG44, or a 1-1000 mg/d] {[4-methylbenzyl 4'-[trans-4-(guanidine-methyl) cyclohexyl carbonyloxy]biphenyl-4-carboxylate monohydrochloride}, or CAS registry number 178748-55-5, administered to the individual in need thereof at a dose of between about 15 mg to about 50 mg per day, or at about 50 to 500 mg per day, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 50 mg, or 20 mg or more, twice daily (bid) or three times daily (tid);

(viii)

(1) an amoxicillin, (2) a furazolidone, optionally FUROXONE™, DEPENDAL-M™, administered to the individual in need thereof at a dose of between about 50 to about 600 mg/d, and (3) a rifabutin, optionally MYCOBUTIN™, administered to the individual in need thereof at a dose of between about 60 to about 450 mg/d, and optionally the rifabutin dose is ramped up starting at about 40 to about 60 g bid or tid, and optionally rising over 3 days to about 200 to about 450/d, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose as set forth in any of (i) to (vii);

(ix) a therapeutic combination as set forth in Table 1; or (x) any combination of (i) to (ix).

2. A method for treating or preventing *Helicobacter pylori* (*H. pylori*) infection in an individual in need thereof, the method comprising administering to the individual in need thereof a therapeutic combination comprising:

(a) vonoprazan, and (b) a prolonged release formulation of an antibiotic comprising:

(1) amoxicillin wherein optionally the amoxicillin is formulated as amoxicillin/clavulanic acid, and/or (2) an antibiotic selected from the group consisting of clarithromycin, azithromycin, roxithromycin and erythromycin, wherein the vonoprazan is administered in an amount of 10 mg to 1 g per day, and the amoxicillin is administered in an amount of 10 mg to 6 g per day.

3. A method for treating or preventing *Helicobacter pylori* (*H. pylori*) infection in an individual in need thereof, the method comprising administering to the individual in need thereof a therapeutic combination comprising:

(a) a prolonged release microencapsulated and/or multimatrix formulation of vonoprazan, and (b) a prolonged release microencapsulated and/or multimatrix formulation of amoxicillin wherein optionally the amoxicillin is formulated as amoxicillin/clavulanic acid, or (c) a prolonged release microencapsulated and/or multimatrix formulation of vonoprazan and amoxicillin wherein optionally the amoxicillin is formulated as amoxicillin/ clavulanic acid, wherein the vonoprazan is administered in an amount of 10 mg to 1 g per day, and the amoxicillin is administered in an amount of 1 g to 6 g per day.

4. A method for treating or preventing *Helicobacter pylori* (*H. pylori*) infection in an individual in need thereof, the method comprising administering to the individual in need thereof a therapeutic combination comprising:

(a) vonoprazan, (b) a proton pump inhibitor, and (c) at least one antibiotic selected from the group consisting of amoxicillin, wherein optionally the amoxicillin is formulated as amoxicillin/clavulanic acid, ampicillin, pivampicillin, hetacillin, bacampicillin, metampicillin, talampicillin, epicillin, a macrolide antibiotic, furazolidone, ciprofloxacin, levofloxacin, tetracycline, a nitroimidazole antibiotic, bismuth, an ansamycin antibiotic, and nitazoxanide, wherein optionally the proton pump inhibitor is selected from the group consisting of omeprazole; pantoprazole; esomeprazole, lansoprazole, and rabeprazole, wherein optionally the macrolide antibiotic is selected from the group consisting of azithromycin, clarithromycin, erythromycin, fidaxomicin, and telithromycin, wherein optionally the nitroimidazole antibiotic is selected from the group consisting of metronidazole, tinidazole, and secnidazole, wherein optionally the ansamycin antibiotic is selected from the group consisting of rifabutin, rifampicin, rifapentin, and rifamixin.

5. A method for treating or preventing *Helicobacter pylori* (*H. pylori*) infection in an individual in need thereof, the method comprising administering to the individual in need thereof a therapeutic combination comprising
(i) amoxicillin, vonoprazan, furazolidone, and rifabutin;
(ii) amoxicillin, vonoprazan, bismuth, furazolidone, rifabutin;
(iii) amoxicillin, vonoprazan, bismuth, levofloxacin, rifabutin;
(iv) amoxicillin, vonoprazan, levofloxacin, rifabutin;
(v) amoxicillin, vonoprazan, bismuth, levofloxacin, furazolidone, rifabutin;
(v) amoxicillin, vonoprazan, bismuth, tetracycline, rifabutin;
(vi) metronidazole, vonoprazan, bismuth, tetracycline, rifabutin;
(v) vonoprazan, bismuth, levofloxacin, rifabutin; or
(vi) amoxicillin, vonoprazan, furazolidone, rifabutin, bismuth, and nitazoxanide,
wherein optionally the amoxicillin is formulated as amoxicillin/clavulanic acid.

6. The method of any one of the preceding forms, wherein the therapeutic combination is administered to the individual in need thereof for about 2, 3, 4, 5, 6, 7, 8, 9, 10, 11, 12, 13 or 14 or more days.

7. The method of any one of the preceding forms, wherein the therapeutic combination is, is contained in or comprises a formulation, a pharmaceutical preparation or a pharmaceutical composition.

8. The method of any one of the preceding forms, wherein the vonoprazan or vonoprazan fumarate, or the 5-(2-fluorophenyl)-1-(pyridin-3-ylsulfonyl)-1H-pyrrol-3-yl)-N-methylmethanamine monofumarate, or the 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof:
(a) at a unit dosage of between about 5 mg to about 200 mg per day, or
(b) in a unit dosage form of between about 10 mg and 200 mgm, or between about between about 40 mg and 100 mgm, or is about 10, 20, 30, 40, 50, 60, 70, 75, 80, 90 or 100 mg per unit dose,
which optionally can be administered once a day, bid or tid, or four times a day, five times a day or six times a day or more, regimen.

9. The method of any one of the preceding forms, wherein therapeutic combination, or the formulation, the pharmaceutical or the pharmaceutical preparation, is formulated as a chewable delivery vehicle, a gum, a gummy, a candy, a lozenge, an ice cream or an ice, or a yogurt.

10. The method of any one of the preceding forms, wherein therapeutic combination, or the formulation, the pharmaceutical or the pharmaceutical preparation, further comprises a flavoring or a sweetening agent, an aspartamine, a stevia, monk fruit, a sucralose, a saccharin, a cyclamate, a xylitol, a vanilla, an artificial vanilla or chocolate or strawberry flavor, an artificial chocolate essence, or a mixture or combination thereof.

11. The method of any one of the preceding forms, wherein therapeutic combination, or the formulation, the pharmaceutical or the pharmaceutical preparation, further comprises a preservative, a benzoic acid or a potassium sorbate.

12. The method of any one of the preceding forms, wherein therapeutic combination, or the formulation, the pharmaceutical or the pharmaceutical preparation, further comprises, or has added to: at least one probiotic or prebiotic, wherein optionally the prebiotic comprises an inulin, lactulose, extracts of artichoke, chicory root, oats, barley, various legumes, garlic, kale, beans or flax or an herb, wherein optionally the probiotic comprises a cultured or stool-extracted microorganism or bacteria, or a bacterial component, and optionally the bacteria or bacterial component comprises or is derived from a *Saccharomyces boulardii*, *Bacteroidetes*, a *Firmicutes*, a *Lactobacilli*, a *Bifidobacteria*, an *E. coli*, a *Strep fecalis* and equivalents.

13. The method of any one of the preceding forms, wherein therapeutic combination, or the formulation, the pharmaceutical or the pharmaceutical preparation, further comprises, or has added to: at least one congealing agent, wherein optionally the congealing agent comprises an arrowroot or a plant starch, a powdered flour, a powdered potato or potato starch, an absorbant polymer, an Absorbable Modified Polymer, and/or a corn flour or a corn starch.

14. The method of any one of the preceding forms, wherein therapeutic combination, or the formulation, the pharmaceutical or the pharmaceutical preparation, further comprises an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient.

15. The method of any one of the preceding forms, wherein therapeutic combination, or the formulation, the pharmaceutical or the pharmaceutical preparation, further comprises, or has added to: at least one Biofilm Disrupting Compound, wherein optionally the biofilm disrupting compound comprises an enzyme, a deoxyribonuclease (DNase), N-acetylcysteine, an auranofin, an alginate lyase, glycoside hydrolase dispersin B; a Quorum-sensing inhibitor, a ribonucleic acid III inhibiting peptide, *Salvadora persica* extracts, Competence-stimulating peptide, Patulin and penicillic acid; peptides—cathelicidin-derived peptides, small lytic peptide, PTP-7, Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, *Delisea* furanones, N-sulfonyl homoserine lactones or any combination thereof.

16. The method of any one of the preceding forms, wherein therapeutic combination, or the formulation, the pharmaceutical or the pharmaceutical preparation, further comprises, or has added to a statin selected from the group consisting of atorvastatin, fluvastatin, lovastatin, pitavastatin, pravastatin, rosuvastatin, and simvastatin.

17. The method of any one of the preceding forms, wherein therapeutic combination, or the formulation, the pharmaceutical or the pharmaceutical preparation, further comprises, or has added to pronase.

18. The method of any one of the preceding forms, wherein therapeutic combination, or the formulation, the pharmaceutical or the pharmaceutical preparation, is formulated as a delayed or gradual enteric release composition or formulation, and optionally the formulation comprises a gastro-resistant coating designed to dissolve at a pH of 7 in the terminal ileum, e.g., an active ingredient is coated with an acrylic based resin or equivalent, e.g., a poly (meth)acrylate, e.g. a methacrylic acid copolymer B, NF, which dissolves at pH 7 or greater, e.g., comprises a multimatrix (MMX) formulation.

19. The method of any one of the preceding forms, wherein therapeutic combination, or the formulation, the pharmaceutical or the pharmaceutical preparation, is contained in a delivery vehicle, product of manufacture, container, syringe, device or bag.

20. The method of any one of the preceding forms, wherein therapeutic combination, or the formulation, the pharmaceutical or the pharmaceutical preparation, is initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation.

21. A therapeutic combination comprising:
    (a) a composition comprising or consisting of: vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™; and
    (b) an antimicrobial or antibiotic drug or composition comprising or consisting of:
    (i)
        (1) an amoxicillin, formulated for administration to the individual in need thereof at a dose of between about 1 gram (g) to about 2 g twice daily (bid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
        (2) a clarithromycin, optionally BIAXIN™, formulated for administration to the individual in need thereof at a dose of between about 100 mg to about 2 g twice daily,
        wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 20 mg to about 50 mg twice daily (bid), or for about 25 mg or more twice daily (bid);
    (ii)
        (1) an amoxicillin, formulated for administration to the individual in need thereof at a dose of between about 500 gm to about 1 g three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
        (2) a metronidazole, optionally FLAGYL™, METRO™, formulated for administration to the individual in need thereof at a dose of between about 200 mg to about 500 mg three times daily (tid),
        wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 20 mg to about 50 mg three times daily (tid), or for about 25 mg or more three times daily (tid);
    (iii)
        (1) an amoxicillin, formulated for administration to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
        (2) a rifabutin, optionally MYCOBUTIN™, formulated for administration to the individual in need thereof at a dose of between about 50 mg to about 250 mg twice daily (bid) or three times daily (tid),
        wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 5 mg to about 200 mg or more twice daily (bid) or three times daily (tid);
    (iv)
        (1) an amoxicillin, formulated for administration to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
        (2) a levofloxacin, formulated for administration to the individual in need thereof at a dose of between about 100 mg to about 500 mg twice daily (bid) or three times daily (tid),
        wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 5 mg to about 200 mg or more twice daily (bid) or three times daily (tid);
    (v)
        (1) an amoxicillin, formulated for administration to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
        (2) a ciprofloxacin, optionally CILOXAN™, CIPRO™, NEOFLOXIN™, formulated for administration to the individual in need thereof at a dose of between about 100 mg to about 500 mg twice daily (bid) or three times daily (tid), wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 5 mg to about 200 mg or more twice daily (bid) or three times daily (tid);

(vi)
- (1) an amoxicillin, formulated for administration to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
- (2) a moxifloxacin, optionally AVELOX™, VIGAMOX™, MOXEZA™, formulated for administration to the individual in need thereof at a dose of between about 25 mg to about 500 mg per day,
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 5 mg to about 200 mg or more twice daily (bid) or three times daily (tid);

(vii)
- (1) an amoxicillin, a clarithromycin, a metronidazole, a levofloxacin, a ciprofloxacin or a moxifloxacin, formulated for administration to the individual in need thereof at a dose as set forth in any of steps (i) to (vi), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
- (2) a TG44, or a 1-1000 mg/d] {[4-methylbenzyl 4'-[trans-4-(guanidine-methyl) cyclohexyl carbonyloxy]biphenyl-4-carboxylate monohydrochloride}, or CAS registry number 178748-55-5, formulated for administration to the individual in need thereof at a dose of between about 15 mg to about 50 mg per day, or at about 50 to 500 mg per day,
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose of between 5 mg to about 50 mg, or 20 mg or more, twice daily (bid) or three times daily (tid);

(viii)
- (1) an amoxicillin,
- (2) a furazolidone, optionally FUROXONE™, DEPENDAL-M™, formulated for administration to the individual in need thereof at a dose of between about 50 to about 600 mg/d, and
- (3) a rifabutin, optionally MYCOBUTIN™, formulated for administration to the individual in need thereof at a dose of between about 60 to about 450 mg/d, and optionally the rifabutin dose is ramped up starting at about 40 to about 60 g bid or tid, and optionally rising over 3 days to about 200 to about 450/d,
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration to the individual in need thereof at a dose as set forth in any of (i) to (vii);

(ix) a therapeutic combination as set forth in Table 1; or (x) any combination of (i) to (ix).

22. A kit or product of manufacture comprising a therapeutic combination of form 21, or a therapeutic combination of any of the preceding forms.

23. Use of a therapeutic combination of form 21, or a therapeutic combination of any of the preceding forms, or a kit or product of manufacture of form 22, in the manufacture of a medicament.

24. A therapeutic combination as set forth in any one of the preceding forms for use in treating, ameliorating, reversing and/or preventing (acting as a prophylaxis) a *Helicobacter pylori* (*H. pylori*) infection in an individual in need thereof.

In a second aspect, forms of the invention described herein include the following:

1. Use of:
(a) a composition comprising or consisting of: vonoprazan or a vonoprazan fumarate, or a 5-(2-fluorophenyl)-1-(pyridin-3-ylsulfonyl)- 1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™; and
(b) an antimicrobial or antibiotic drug or composition comprising or consisting of:

(i)
- (1) an amoxicillin, formulated for administration at a dose of between about 1 gram (g) to about 2 g twice daily (bid), optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
- (2) a clarithromycin, optionally BIAXIN™, formulated for administration at a dose of between about 100 mg to about 2 g twice daily,
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration at a dose of between 20 mg to about 50 mg twice daily (bid), or for about 25 mg or more twice daily (bid);

(ii)
- (1) an amoxicillin, formulated for administration at a dose of between about 500 gm to about 1 g three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
- (2) a metronidazole, optionally FLAGYL™, METRO™, formulated for administration at a dose of between about 200 mg to about 500 mg three times daily (tid),
wherein the vonoprazan or a vonoprazan fumarate, or a 5-(2-fluorophenyl)-1-(pyridin-3-ylsulfonyl)-1H-pyrrol-3- yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration at a dose of between 20 mg to about 50 mg three times daily (tid), or for about 25 mg or more three times daily (tid);

(iii)
(1) an amoxicillin, formulated for administration at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a rifabutin, optionally MYCOBUTIN™, formulated for administration at a dose of between about 50 mg to about 250 mg twice daily (bid) or three times daily (tid),
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration at a dose of between 5 mg to about 200 mg or more twice daily (bid) or three times daily (tid);

(iv)
(1) an amoxicillin, formulated for administration at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a levofloxacin, formulated for administration at a dose of between about 100 mg to about 500 mg twice daily (bid) or three times daily (tid),
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration at a dose of between 5 mg to about 200 mg or more twice daily (bid) or three times daily (tid);

(v)
(1) an amoxicillin, formulated for administration at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a ciprofloxacin, optionally CILOXAN™, CIPRO™, NEOFLOXIN™, administered to the individual in need thereof at a dose of between about 100 mg to about 500 mg twice daily (bid) or three times daily (tid),
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(vi)
(1) an amoxicillin, administered to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a moxifloxacin, optionally AVELOX™, VIGAMOX™, MOXEZA™, administered to the individual in need thereof at a dose of between about 25 mg to about 500 mg per day,
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(vii)
(1) an amoxicillin, a clarithromycin, a metronidazole, a levofloxacin, a ciprofloxacin or a moxifloxacin, administered to the individual in need thereof at a dose as set forth in any of steps (i) to (vi), optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
(2) a TG44, or a 1-1000 mg/d] {[4-methylbenzyl 4'-[trans-4-(guanidine-methyl) cyclohexyl carbonyloxy]biphenyl-4-carboxylate monohydrochloride}, or CAS registry number 178748-55-5, administered to the individual in need thereof at a dose of between about 15 mg to about 50 mg per day, or at about 50 to 500 mg per day,
wherein the vonoprazan or a vonoprazan fumarate, or a 5-(2-fluorophenyl)-1-(pyridin-3-ylsulfonyl)- 1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 50 mg, or 20 mg or more, twice daily (bid) or three times daily (tid);

(viii)
(1) an amoxicillin,
(2) a furazolidone, optionally FUROXONE™, DEPENDAL-M™, administered to the individual in need thereof at a dose of between about 50 to about 600 mg/d, and
(3) a rifabutin, optionally MYCOBUTIN™, administered to the individual in need thereof at a dose of between about 60 to about 450 mg/d, and optionally the rifabutin dose is ramped up starting at about 40 to about 60 g bid or tid, and optionally rising over 3 days to about 200 to about 450/d,
wherein the vonoprazan or a vonoprazan fumarate, or a 5-(2-fluorophenyl)-1-(pyridin-3-ylsulfonyl)- 1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose as set forth in any of (i) to (vii);
(ix) a therapeutic combination as set forth in Table 1; or
(x) any combination of (i) to (ix),
in the manufacture of a medicament for treating or preventing *Helicobacter pylori* (*H. pylori*) infection in an individual in need thereof.

2. Use of a therapeutic combination comprising:
(a) vonoprazan, and
(b) a prolonged release formulation of an antibiotic comprising:
(1) amoxicillin wherein optionally the amoxicillin is formulated as amoxicillin/clavulanic acid, and/or
(2) an antibiotic selected from the group consisting of clarithromycin, azithromycin, roxithromycin and erythromycin,
in the manufacture of a medicament for treating or preventing *Helicobacter pylori* (*H. pylori*) infection in an individual in need thereof,
wherein the vonoprazan is formulated for administration in an amount of 10 mg to 1 g per day, and the amoxicillin is formulated for administration in an amount of 10 mg to 6 g per day.

3. Use of a therapeutic combination comprising
(a) a prolonged release microencapsulated and/or multimatrix formulation of vonoprazan, and
(b) a prolonged release microencapsulated and/or multimatrix formulation of amoxicillin wherein optionally the amoxicillin is formulated as amoxicillin/clavulanic acid, or
(c) a prolonged release microencapsulated and/or multimatrix formulation of vonoprazan and amoxicillin wherein optionally the amoxicillin is formulated as amoxicillin/clavulanic acid,
in the manufacture of a medicament for treating or preventing *Helicobacter pylori* (*H. pylori*) infection in an individual in need thereof,
wherein the vonoprazan is administered in an amount of 10 mg to 1 g per day, and the amoxicillin is administered in an amount of 1 g to 6 g per day.

4. Use of a therapeutic combination comprising:
(a) vonoprazan,
(b) a proton pump inhibitor, and
(c) at least one antibiotic selected from the group consisting of amoxicillin, wherein optionally the amoxicillin is formulated as amoxicillin/clavulanic acid, ampicillin, pivampicillin, hetacillin, bacampicillin, metampicillin, talampicillin, epicillin, a macrolide antibiotic, furazolidone, ciprofloxacin, levofloxacin, tetracycline, a nitroimidazole antibiotic, bismuth, an ansamycin antibiotic, and nitazoxanide,
wherein optionally the proton pump inhibitor is selected from the group consisting of omeprazole; pantoprazole; esomeprazole, lansoprazole, and rabeprazole,
wherein optionally the macrolide antibiotic is selected from the group consisting of azithromycin, clarithromycin, erythromycin, fidaxomicin, and telithromycin,
wherein optionally the nitroimidazole antibiotic is selected from the group consisting of metronidazole, tinidazole, and secnidazole,
wherein optionally the ansamycin antibiotic is selected from the group consisting of rifabutin, rifampicin, rifapentin, and rifamixin,
in the manufacture of a medicament for treating or preventing *Helicobacter pylori* (*H. pylori*) infection in an individual in need thereof.

5. Use of a therapeutic combination comprising
(i) amoxicillin, vonoprazan, furazolidone, and rifabutin;
(ii) amoxicillin, vonoprazan, bismuth, furazolidone, rifabutin;
(iii) amoxicillin, vonoprazan, bismuth, levofloxacin, rifabutin;
(iv) amoxicillin, vonoprazan, levofloxacin, rifabutin;
(v) amoxicillin, vonoprazan, bismuth, levofloxacin, furazolidone, rifabutin;
(v) amoxicillin, vonoprazan, bismuth, tetracycline, rifabutin;
(vi) metronidazole, vonoprazan, bismuth, tetracycline, rifabutin;
(v) vonoprazan, bismuth, levofloxacin, rifabutin; or
(vi) amoxicillin, vonoprazan, furazolidone, rifabutin, bismuth, and nitazoxanide,
wherein optionally the amoxicillin is formulated as amoxicillin/clavulanic acid, in the manufacture of a medicament for treating or preventing *Helicobacter pylori* (*H. pylori*) infection in an individual in need thereof.

6. The use of any one of the preceding forms, wherein the therapeutic combination is formulated for administration to the individual in need thereof for about 2, 3, 4, 5, 6, 7, 8, 9, 10, 11, 12, 13 or 14 or more days.

7. The use of any one of the preceding forms, wherein the therapeutic combination is, is contained in or comprises a formulation, a pharmaceutical preparation or a pharmaceutical composition.

8. The use of any of the preceding forms, wherein the vonoprazan or vonoprazan fumarate, or the 5-(2-fluorophenyl)-1-(pyridin-3-ylsulfonyl)-1H-pyrrol-3-yl)-N-methylmethanamine monofumarate, or the 1-(5-(2-fluorophenyl)-1-(pyridin-3-ylsulfonyl)-1H-pyrrol-3-yl)-N-methyl-methanamine fumarate), optionally TAKECAB™, is formulated for administration:
(a) at a unit dosage of between about 5 mg to about 200 mg per day, or
(b) in a unit dosage form of between about 10 mg and 200 mgm, or between about between about 40 mg and 100 mgm, or is about 10, 20, 30, 40, 50, 60, 70, 75, 80, 90 or 100 mg per unit dose,
which optionally is formulated for administration once a day, bid or tid, or a four times a day, five times a day or six times a day or more.

9. The use of any of the preceding forms, wherein therapeutic combination, or the formulation, the pharmaceutical or the pharmaceutical preparation, is formulated as a chewable delivery vehicle, a gum, a gummy, a candy, a lozenge, an ice cream or an ice, or a yogurt.

10. The use of any of the preceding forms, wherein the medicament further comprises a flavoring or a sweetening agent, an aspartamine, a stevia, monk fruit, a sucralose, a saccharin, a cyclamate, a xylitol, a vanilla, an artificial vanilla or chocolate or strawberry flavor, an artificial chocolate essence, or a mixture or combination thereof.

11. The use of any of the preceding forms, wherein the medicament further comprises a preservative, a benzoic acid or a potassium sorbate.

12. The use of any of the preceding forms, wherein the medicament further comprises at least one probiotic or prebiotic, wherein optionally the prebiotic comprises an inulin, lactulose, extracts of artichoke, chicory root, oats, barley, various legumes, garlic, kale, beans or flacks or an herb, wherein optionally the probiotic comprises a cultured or stool-extracted microorganism or bacteria, or a bacterial component, and optionally the bacteria or bacterial component comprises or is derived from a *Bacteroidetes*, a *Firmicutes*, a *Lactobacilli*, a *Bifidobacteria*, an *E. coli*, a *Strep fecalis* and equivalents.

13. The use of any of the preceding forms, wherein the medicament further comprises at least one congealing agent, wherein optionally the congealing agent comprises an arrowroot or a plant starch, a powdered flour, a powdered potato or potato starch, an absorbant polymer, an Absorbable Modified Polymer, and/or a corn flour or a corn starch.
14. The use of any of the preceding forms, wherein the medicament further comprises an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient.
15. The use of any of the preceding forms, wherein the medicament further comprises at least one Biofilm Disrupting Compound, wherein optionally the biofilm disrupting compound comprises an enzyme, a deoxyribonuclease (DNase), N-acetylcysteine, an auranofin, an alginate lyase, glycoside hydrolase dispersin B; a Quorum-sensing inhibitor, a ribonucleic acid III inhibiting peptide, *Salvadora persica* extracts, Competence-stimulating peptide, Patulin and penicillic acid; peptides—cathelicidin-derived peptides, small lytic peptide, PTP-7, Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, *Delisea* furanones, N-sulfonyl homoserine lactones or any combination thereof.
16. The use of any of the preceding forms, wherein the medicament is formulated as a delayed or gradual enteric release composition or formulation, and optionally the formulation comprises a gastro-resistant coating designed to dissolve at a pH of 7 in the terminal ileum, e.g., an active ingredient is coated with an acrylic based resin or equivalent, e.g., a poly(meth)acrylate, e.g. a methacrylic acid copolymer B, NF, which dissolves at pH 7 or greater, e.g., comprises a multimatrix (MMX) formulation.
17. The use of any of the preceding forms, wherein the medicament is contained in a delivery vehicle, product of manufacture, container, syringe, device or bag.
18. The use of any of the preceding forms, wherein the medicament is initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation.
19. The use of any one of the preceding forms, wherein therapeutic combination, or the formulation, the pharmaceutical or the pharmaceutical preparation, further comprises, or has added to a statin selected from the group consisting of atorvastatin, fluvastatin, lovastatin, pitavastatin, pravastatin, rosuvastatin, and simvastatin.
20. The use of any one of the preceding forms, wherein therapeutic combination, or the formulation, the pharmaceutical or the pharmaceutical preparation, further comprises, or has added to pronase.

In a third aspect, forms of the invention described herein include the following:
1. A combination of:
 (a) a composition comprising or consisting of: vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™; and
 (b) an antimicrobial or antibiotic drug or composition comprising or consisting of:
  (i)
   (1) an amoxicillin, formulated for administration at a dose of between about 1 gram (g) to about 2 g twice daily (bid), optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
   (2) a clarithromycin, optionally BIAXIN™, formulated for administration at a dose of between about 100 mg to about 2 g twice daily,
  wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration at a dose of between 20 mg to about 50 mg twice daily (bid), or for about 25 mg or more twice daily (bid);
  (ii)
   (1) an amoxicillin, formulated for administration at a dose of between about 500 gm to about 1 g three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
   (2) a metronidazole, optionally FLAGYL™, METRO™, formulated for administration at a dose of between about 200 mg to about 500 mg three times daily (tid),
  wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration at a dose of between 20 mg to about 50 mg three times daily (tid), or for about 25 mg or more three times daily (tid);
  (iii)
   (1) an amoxicillin, formulated for administration at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and
   (2) a rifabutin, optionally MYCOBUTIN™, formulated for administration at a dose of between about 50 mg to about 250 mg twice daily (bid) or three times daily (tid),
  wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration at a dose of between 5 mg to about 200 mg or more twice daily (bid) or three times daily (tid);
  (iv)
   (1) an amoxicillin, formulated for administration at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and (2) a levofloxacin, formulated for administration at a dose of between about 100 mg to about 500 mg twice daily (bid) or three times daily (tid), wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is formulated for administration at a dose of between 5 mg to about 200 mg or more twice daily (bid) or three times daily (tid);

(v)
(1) an amoxicillin, formulated for administration at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and (2) a ciprofloxacin, optionally CILOXAN™, CIPRO™, NEOFLOXIN™, administered to the individual in need thereof at a dose of between about 100 mg to about 500 mg twice daily (bid) or three times daily (tid), wherein the vonoprazan or a vonoprazan fumarate, or a 5-(2-fluorophenyl)-1-(pyridin-3-ylsulfonyl)-1H-pyrrool-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(vi)
(1) an amoxicillin, administered to the individual in need thereof at a dose of between about 250 gm to about 1 g twice daily (bid) or three times daily (tid), and optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and (2) a moxifloxacin, optionally AVELOX™, VIGAMOX™, MOXEZA™, administered to the individual in need thereof at a dose of between about 25 mg to about 500 mg per day, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 200 mg or more twice daily (bid) or three times daily (tid);

(vii)
(1) an amoxicillin, a clarithromycin, a metronidazole, a levofloxacin, a ciprofloxacin or a moxifloxacin, administered to the individual in need thereof at a dose as set forth in any of steps (i) to (vi), optionally the amoxicillin is formulated as amoxicillin/ clavulanic acid, also known as co-amoxiclav, or is optionally ACTIMOXI™, ALPHAMOX™, AMOCLA™, TYCIL™, AMOXIL™, TRIMOX™; and (2) a TG44, or a 1-1000 mg/d] {[4-methylbenzyl 4'-[trans-4-(guanidine-methyl) cyclohexyl carbonyloxy]biphenyl-4-carboxylate monohydrochloride}, or CAS registry number 178748-55-5, administered to the individual in need thereof at a dose of between about 15 mg to about 50 mg per day, or at about 50 to 500 mg per day, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose of between 5 mg to about 50 mg, or 20 mg or more, twice daily (bid) or three times daily (tid);

(viii)
(1) an amoxicillin,
(2) a furazolidone, optionally FUROXONE™, DEPENDAL-M™, administered to the individual in need thereof at a dose of between about 50 to about 600 mg/d, and
(3) a rifabutin, optionally MYCOBUTIN™, administered to the individual in need thereof at a dose of between about 60 to about 450 mg/d, and optionally the rifabutin dose is ramped up starting at about 40 to about 60 g bid or tid, and optionally rising over 3 days to about 200 to about 450/d, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), optionally TAKECAB™, is administered to the individual in need thereof at a dose as set forth in any of (i) to (vii);

(ix) a therapeutic combination as set forth in Table 1; or
(x) any combination of (i) to (ix), for use in treating or preventing *Helicobacter pylori* (*H. pylori*) infection in an individual in need thereof.

2. A therapeutic combination comprising:
(a) vonoprazan, and
(b) a prolonged release formulation of an antibiotic comprising:
(1) amoxicillin wherein optionally the amoxicillin is formulated as amoxicillin/clavulanic acid, and/or
(2) an antibiotic selected from the group consisting of clarithromycin, azithromycin, roxithromycin and erythromycin, wherein the vonoprazan is formulated for administration in an amount of 10 mg to 1 g per day, and the amoxicillin is formulated for administration in an amount of 10 mg to 6 g per day, for use in treating or preventing *Helicobacter pylori* (*H. pylori*) infection in an individual in need thereof.

3. A therapeutic combination comprising:
(a) a prolonged release microencapsulated and/or multimatrix formulation of vonoprazan, and
(b) a prolonged release microencapsulated and/or multimatrix formulation of amoxicillin wherein optionally the amoxicillin is formulated as amoxicillin/clavulanic acid, or
(c) a prolonged release microencapsulated and/or multimatrix formulation of vonoprazan and amoxicillin wherein optionally the amoxicillin is formulated as amoxicillin/ clavulanic acid, wherein the vonoprazan is formulated for administration in an amount of 10 mg to 1 g per day, and the amoxicillin is formulated for administration in an amount of 1 g to 6 g per day, for use in treating or preventing *Helicobacter pylori* (*H. pylori*) infection in an individual in need thereof.

4. A therapeutic combination comprising:
(a) vonoprazan,
(b) a proton pump inhibitor, and
(c) at least one antibiotic selected from the group consisting of amoxicillin, wherein optionally the amoxicillin is formulated as amoxicillin/clavulanic acid, ampicillin, pivampicillin, hetacillin, bacampicillin, metampicillin, talampicillin, epicillin, a macrolide antibiotic, furazolidone, ciprofloxacin, levofloxacin, tetracycline, a nitroimidazole antibiotic, bismuth, an ansamycin antibiotic, and nitazoxanide,
wherein optionally the proton pump inhibitor is selected from the group consisting of omeprazole; pantoprazole; esomeprazole, lansoprazole, and rabeprazole,
wherein optionally the macrolide antibiotic is selected from the group consisting of azithromycin, clarithromycin, erythromycin, fidaxomicin, and telithromycin,
wherein optionally the nitroimidazole antibiotic is selected from the group consisting of metronidazole, tinidazole, and secnidazole,
wherein optionally the ansamycin antibiotic is selected from the group consisting of rifabutin, rifampicin, rifapentin, and rifamixin,
for use in treating or preventing *Helicobacter pylori* (*H. pylori*) infection in an individual in need thereof.

5. A therapeutic combination comprising
(i) amoxicillin, vonoprazan, furazolidone, and rifabutin;
(ii) amoxicillin, vonoprazan, bismuth, furazolidone, rifabutin;
(iii) amoxicillin, vonoprazan, bismuth, levofloxacin, rifabutin;
(iv) amoxicillin, vonoprazan, levofloxacin, rifabutin;
(v) amoxicillin, vonoprazan, bismuth, levofloxacin, furazolidone, rifabutin;
(v) amoxicillin, vonoprazan, bismuth, tetracycline, rifabutin;
(vi) metronidazole, vonoprazan, bismuth, tetracycline, rifabutin;
(v) vonoprazan, bismuth, levofloxacin, rifabutin; or
(vi) amoxicillin, vonoprazan, furazolidone, rifabutin, bismuth, and nitazoxanide,
wherein optionally the amoxicillin is formulated as amoxicillin/clavulanic acid,
for use in treating or preventing *Helicobacter pylori* (*H. pylori*) infection in an individual in need thereof.

6. The combination of any one of the preceding forms, wherein the therapeutic combination is formulated for administration to the individual in need thereof for about 2, 3, 4, 5, 6, 7, 8, 9, 10, 11, 12, 13 or 14 or more days.

7. The combination of any one of the preceding forms, wherein the therapeutic combination is, is contained in or comprises a formulation, a pharmaceutical preparation or a pharmaceutical composition.

8. The combination of any of the preceding forms, wherein the vonoprazan or vonoprazan fumarate, or the 5-(2-fluorophenyl)-1-(pyridin-3-ylsulfonyl)-1H-pyrrol-3-yl)-N-methylmethanamine monofumarate, or the 1-(5-(2-fluorophenyl)-1-(pyridin-3-ylsulfonyl)-1H-pyrrol-3-yl)-N-methyl-methanamine fumarate), optionally TAKECAB™, is formulated for administration:
(a) at a unit dosage of between about 5 mg to about 200 mg per day, or
(b) in a unit dosage form of between about 10 mg and 200 mgm, or between about between about 40 mg and 100 mgm, or is about 10, 20, 30, 40, 50, 60, 70, 75, 80, 90 or 100 mg per unit dose,
which optionally is formulated for administration once a day, bid or tid, or a four times a day, five times a day or six times a day or more.

9. The combination of any of the preceding forms, formulated as a chewable delivery vehicle, a gum, a gummy, a candy, a lozenge, an ice cream or an ice, or a yogurt.

10. The combination of any of the preceding forms, further comprising a flavoring or a sweetening agent, an aspartamine, a stevia, monk fruit, a sucralose, a saccharin, a cyclamate, a xylitol, a vanilla, an artificial vanilla or chocolate or strawberry flavor, an artificial chocolate essence, or a mixture or combination thereof.

11. The combination of any of the preceding forms, further comprising a preservative, a benzoic acid or a potassium sorbate.

12. The combination of any of the preceding forms, further comprising at least one probiotic or prebiotic, wherein optionally the prebiotic comprises an inulin, lactulose, extracts of artichoke, chicory root, oats, barley, various legumes, garlic, kale, beans or flacks or an herb, wherein optionally the probiotic comprises a cultured or stool-extracted microorganism or bacteria, or a bacterial component, and optionally the bacteria or bacterial component comprises or is derived from a *Bacteroidetes*, a *Firmicutes*, a *Lactobacilli*, a *Bifidobacteria*, an *E. coli*, a *Strep fecalis* and equivalents.

13. The combination of any of the preceding forms, further comprising at least one congealing agent, wherein optionally the congealing agent comprises an arrowroot or a plant starch, a powdered flour, a powdered potato or potato starch, an absorbant polymer, an Absorbable Modified Polymer, and/or a corn flour or a corn starch.

14. The combination of any of the preceding forms, further comprising an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient.

15. The combination of any of the preceding forms, further comprising at least one Biofilm Disrupting Compound, wherein optionally the biofilm disrupting compound comprises an enzyme, a deoxyribonuclease (DNase), N-acetylcysteine, an auranofin, an alginate lyase, glycoside hydrolase dispersin B; a Quorum-sensing inhibitor, a ribonucleic acid III inhibiting peptide, *Salvadora persica* extracts, Competence-stimulating peptide, Patulin and penicillic acid; peptides—cathelicidin-derived peptides, small lytic peptide, PTP-7, Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, *Delisea* furanones, N-sulfonyl homoserine lactones or any combination thereof.

16. The combination of any of the preceding forms, formulated as a delayed or gradual enteric release composition or formulation, and optionally the formulation comprises a gastro-resistant coating designed to dissolve at a pH of 7 in the terminal ileum, e.g., an active ingredient is coated with an acrylic based resin or equivalent, e.g., a poly (meth)acrylate, e.g. a methacrylic acid copolymer B, NF, which dissolves at pH 7 or greater, e.g., comprises a multimatrix (MMX) formulation.

17. The combination of any of the preceding forms, contained in a delivery vehicle, product of manufacture, container, syringe, device or bag.

18. The combination of any of the preceding forms, wherein the combination is initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation.

DETAILED DESCRIPTION

In alternative embodiments, provided are therapeutic combinations (including formulations, pharmaceutical preparations or pharmaceutical compositions) for treating, ameliorating, reversing and/or preventing (acting as a prophylaxis) a *Helicobacter pylori* (*H. pylori*) infection in an individual in need thereof, including products of manufacture and kits, for practicing methods as provided herein.

In alternative embodiments, therapeutic combinations, formulations, pharmaceutical preparations or pharmaceutical compositions as provided herein use vonoprazan to improve efficacy in novel combinations to achieve close to 100% eradication of *Helicobacter pylori* (*H. pylori*) infections; and this significant breakthrough is particularly relevant for those individuals in need thereof who have previously failed eradication of *H. pylori,* or at least have failed to get any or clinically sufficient resolution of an *H. pylori* infection and/or symptoms associated with *H. pylori* infection.

In alternative embodiments, therapeutic combinations, formulations, pharmaceutical preparations or pharmaceutical compositions as provided herein use the unexpected bactericidal activity of the new compositions mitigating resistance which give new life to otherwise failing of lagging *H. pylori* (HP)-eradication protocols, as discussed above. By adding vonoprazan the resistance of *H. pylori* is clearly reduced, and while the invention is not limited by any particular mechanism of action, this may be due to vonoprazan causing a much greater availability of amoxicillin in the stomach, leading to much higher eradication rates across numerous trials, some reaching nearly 100% eradication. Additionally, vonoprozan itself has some endogenous anti-microbial activity.

In alternative embodiments, provided are therapeutic combinations (including formulations, pharmaceutical preparations or pharmaceutical compositions) which use vonoprazan in a dose of between about 5 mg to about 200 mg per day, in conjunction with various other antibiotics or other antimicrobials or drugs.

In alternative embodiments, provided are therapeutic combinations (including formulations, pharmaceutical preparations or pharmaceutical compositions) which are more effective than the standard amoxicillin, clarithromycin, and vonoprazan protocol. In alternative embodiments, provided are therapeutic combinations and regimens comprising or consisting of an amoxicillin, clarithromycin, and vonoprazan that achieve significantly higher eradication than existing protocols, where exemplary therapeutic combinations and drug regimens comprise, for example:

amoxicillin is used at a dose of about 1 g to about 2 g twice daily, in conjunction with clarithromycin at about 100 mg through to about 2 g twice daily, with vonoprazan at a dose of about 25 mg or more twice daily, for about 5 or more days. Another combination is the use of amoxicillin and clarithromycin in doses listed above but administered 3 times daily and vonoprazan also 3 times daily, in doses between about 5 mg to about 200 mg three times daily for 5 or more days;

a 7 day, or 5 or more days, course of vonoprazan at about 20 mg or more three times daily, metronidazole at about 200 to about 500 mg three times daily and amoxicillin at about 500 mg to about 1 g three times daily, which can achieve close to 100% eradiation rate in those people who are not allergic to amoxicillin or metronidazole given for 5 or more days; this can be used as First Line or subsequent therapy composition;

vonoprazan 2 to 3 times daily in doses of about 5 mg to about 200 mg/d, together with rifabutin 2 to 3 times daily at about 50 mg to about 250 mg, and amoxicillin at about 250 mg to about 1 g 2 to 3 times daily; this is also a very effective First Line or salvage/rescue therapy in those patients who have previously failed eradication;

a combination taken for 5 or more days, is that of similar doses as given above of amoxicillin and vonoprazan but also combined with either levofloxacin from between 100 to 500 mg 2 to 3 times per day or ciprofloxacin at about 100 to about 500 mg 2 to 3 times/day (d), or moxifloxacin at about 25 to about 500 mg/d;

vonoprazan at about 20 mg or more 2 to 3 times/day combined with the new anti HP agent TG44 (1-1000 mg/d] {[4-methylbenzyl 4'-[trans-4-(guanidinomethyl) cyclohexyl carbonyloxy]biphenyl-4-carboxylate monohydrochloride} [CAS registry number 178748-55-5] twice or three times daily and the protocol can include the following: TG44 can be used alone with vonoprazan, or combined with amoxicillin, clarithromycin, metronidazole, levofloxacin, ciprofloxacin or moxifloxacin in the doses given above, optionally for about 5 or more days.

Additional exemplary therapeutic combinations that can be used 2 to 3 times/d protocols, optionally taken for 5 or more days, include:

amoxicillin and vanoprazan, with furazolidone at about 50 to about 600 mg/d, and rifabutin at about 60 to about 450 mg/d; the rifabutin dose can be ramped up to prevent fevers, for example, starting at about 40 to about 60 g bid or tid, and optionally rising over 3 days to about 200 to about 450/d;

additional exemplary therapeutic combinations that can be used 2 to 3 times/d protocols, optionally taken for 5 or more days, include those as set forth in Table 1, below:

TABLE 1

| | A. | | | |
|---|---|---|---|---|
| Times | Amoxicillin 375 mg | Vonoprazan 20 mg | Furazolidone 100 mg | Rifabutin 60 mg |
| | DAY 1 | | | |
| 8 am | 4 Capsules | 1 Capsule | 1 Capsule | 1 Capsule |
| 1 pm | 4 Capsules | 1 Capsule | 1 Capsule | 0 |
| 8 pm | 4 Capsules | 1 Capsule | 1 Capsule | 1 Capsule |

TABLE 1-continued

| | | DAY 2 | | |
|---|---|---|---|---|
| 8 am | 4 Capsules | 1 Capsule | 1 Capsule | 1 Capsule |
| 1 pm | 4 Capsules | 1 Capsule | 1 Capsule | 0 |
| 8 pm | 4 Capsules | 1 Capsule | 1 Capsule | 2 Capsules |

| | | DAY 3 TO DAY 14 | | |
|---|---|---|---|---|
| Times | Amoxicillin 375 mg | Vonoprazan 20 mg | Furazolidone 100 mg | Rifabutin 120 mg |
| 8 am | 4 Capsules | 1 Capsule | 1 Capsule | 1 Capsule |
| 1 pm | 4 Capsules | 1 Capsule | 1 Capsule | 0 |
| 8 pm | 4 Capsules | 1 Capsule | 1 Capsule | 1 Capsule |

B.

| Times | Amoxicillin 375 mg | Vonoprazan 20 mg | Bismuth 300 mg | Furazolidone 100 mg | Rifabutin 60 mg |
|---|---|---|---|---|---|
| | | | DAY 1 | | |
| 8 am | 4 Capsules | 1 Capsule | 2 Capsules | 1 Capsule | 1 Capsule |
| 1 pm | 4 Capsules | 1 Capsule | 2 Capsules | 1 Capsule | 0 |
| 8 pm | 4 Capsules | 1 Capsule | 2 Capsules | 1 Capsule | 1 Capsule |
| | | | DAY 2 | | |
| 8 am | 4 Capsules | 1 Capsule | 2 Capsules | 1 Capsule | 1 Capsule |
| 1 pm | 4 Capsules | 1 Capsule | 2 Capsules | 1 Capsule | 0 |
| 8 pm | 4 Capsules | 1 Capsule | 2 Capsules | 1 Capsule | 2 Capsules |

| | | | DAY 3 TO DAY 14 | | |
|---|---|---|---|---|---|
| Times | Amoxicillin 375 mg | Vonoprazan 20 mg | Bismuth 300 mg | Furazolidone 100 mg | Rifabutin 120 mg |
| 8 am | 4 Capsules | 1 Capsule | 2 Capsules | 1 Capsule | 1 Capsule |
| 1 pm | 4 Capsules | 1 Capsule | 2 Capsules | 1 Capsule | 0 |
| 8 pm | 4 Capsules | 1 Capsule | 2 Capsules | 1 Capsule | 1 Capsule |

C.

| Times | Amoxicillin 375 mg | Vonoprazan 20 mg | Bismuth 300 mg | Levofloxacin 375 mg | Rifabutin 60 mg |
|---|---|---|---|---|---|
| | | | DAY 1 | | |
| 8 am | 4 Capsules | 1 Capsule | 2 Capsules | 1 Capsule | 1 Capsule |
| 1 pm | 4 Capsules | 1 Capsule | 2 Capsules | 0 | 0 |
| 8 pm | 4 Capsules | 1 Capsule | 2 Capsules | 2 Capsules | 1 Capsule |
| | | | DAY 2 | | |
| 8 am | 4 Capsules | 1 Capsule | 2 Capsules | 1 Capsule | 1 Capsule |
| 1 pm | 4 Capsules | 1 Capsule | 2 Capsules | 0 | 0 |
| 8 pm | 4 Capsules | 1 Capsule | 2 Capsules | 2 Capsules | 2 Capsules |

| | | | DAY 3 TO 14 | | |
|---|---|---|---|---|---|
| Times | Amoxicillin 375 mg | Vonoprazan 20 mg | Bismuth 300 mg | Levofloxacin 375 mg | Rifabutin 120 mg |
| 8 am | 4 Capsules | 1 Capsule | 2 Capsules | 1 Capsule | 1 Capsule |
| 1 pm | 4 Capsules | 1 Capsule | 2 Capsules | 0 | 0 |
| 8 pm | 4 Capsules | 1 Capsule | 2 Capsules | 2 Capsules | 1 Capsule |

D.

| Times | Amoxicillin 375 mg | Vonoprazan 20 mg | Furazolidone 100 mg | Rifabutin 60 mg |
|---|---|---|---|---|
| | | DAY 1 | | |
| 8 am | 4 Capsules | 1 Capsule | 1 Capsule | 1 Capsule |
| 1 pm | 4 Capsules | 1 Capsule | 1 Capsule | 0 |
| 8 pm | 4 Capsules | 1 Capsule | 1 Capsule | 1 Capsule |

TABLE 1-continued

| | | DAY 2 | | |
|---|---|---|---|---|
| 8 am | 4 Capsules | 1 Capsule | 1 Capsule | 1 Capsule |
| 1 pm | 4 Capsules | 1 Capsule | 1 Capsule | 0 |
| 8 pm | 4 Capsules | 1 Capsule | 1 Capsule | 2 Capsules |

| | | DAY 3 TO DAY 14 | | |
|---|---|---|---|---|
| Times | Amoxicillin 375 mg | Vonoprazan 20 mg | Furazolidone 100 mg | Rifabutin 120 mg |
| 8 am | 4 Capsules | 1 Capsule | 1 Capsule | 1 Capsule |
| 1 pm | 4 Capsules | 1 Capsule | 1 Capsule | 0 |
| 8 pm | 4 Capsules | 1 Capsule | 1 Capsule | 1 Capsule |

E.

| Times | Amoxicillin 375 mg | Vonoprazan 20 mg | Rifabutin 60 mg | Levofloxacin 375 mg |
|---|---|---|---|---|
| 8 am | 4 Capsules | 1 Capsule | 1 Capsule | 1 Capsule |
| 1 pm | 4 Capsules | 1 Capsule | 0 | 0 |
| 8 pm | 4 Capsules | 1 Capsule | 1 Capsule | 2 Capsules |

| | | DAY 2 | | |
|---|---|---|---|---|
| 8 am | 4 Capsules | 1 Capsule | 1 Capsule | 1 Capsule |
| 1 pm | 4 Capsules | 1 Capsule | 0 | 0 |
| 8 pm | 4 Capsules | 1 Capsule | 2 Capsules | 2 Capsules |

| | | DAY 3 TO DAY 14 | | |
|---|---|---|---|---|
| Times | Amoxicillin 375 mg | Vonoprazan 20 mg | Rifabutin 120 mg | Levofloxacin 375 mg |
| 8 am | 4 Capsules | 1 Capsule | 1 Capsule | 1 Capsule |
| 1 pm | 4 Capsules | 1 Capsule | 0 | 0 |
| 8 pm | 4 Capsules | 1 Capsule | 1 Capsule | 2 Capsules |

F.

| Times | Amoxicillin 375 mg | Vonoprazan 20 mg | Bismuth 300 mg | Furazolidone 100 mg | Rifabutin 60 mg |
|---|---|---|---|---|---|
| | | | DAY 1 | | |
| 8 am | 4 Capsules | 1 Capsule | 2 Capsules | 1 Capsule | 1 Capsule |
| 1 pm | 4 Capsules | 1 Capsule | 2 Capsules | 1 Capsule | 0 |
| 8 pm | 4 Capsules | 1 Capsule | 2 Capsules | 1 Capsule | 1 Capsule |
| | | | DAY 2 | | |
| 8 am | 4 Capsules | 1 Capsule | 2 Capsules | 1 Capsule | 1 Capsule |
| 1 pm | 4 Capsules | 1 Capsule | 2 Capsules | 1 Capsule | 0 |
| 8 pm | 4 Capsules | 1 Capsule | 2 Capsules | 1 Capsule | 2 Capsules |

| | | DAY 3 TO DAY 14 | | | |
|---|---|---|---|---|---|
| Times | Amoxicillin 375 mg | Vonoprazan 20 mg | Bismuth 300 mg | Furazolidone 100 mg | Rifabutin 120 mg |
| 8 am | 4 Capsules | 1 Capsule | 2 Capsules | 1 Capsule | 1 Capsule |
| 1 pm | 4 Capsules | 1 Capsule | 2 Capsules | 1 Capsule | 0 |
| 8 pm | 4 Capsules | 1 Capsule | 2 Capsules | 1 Capsule | 1 Capsule |

G.

| Times | Amoxicillin 375 mg | Vonoprazan 20 mg | Bismuth 300 mg | Levofloxacin 375 mg | Rifabutin 60 mg |
|---|---|---|---|---|---|
| | | | DAY 1 | | |
| 8 am | 4 Capsules | 1 Capsule | 2 Capsules | 1 Capsule | 1 Capsule |
| 1 pm | 4 Capsules | 1 Capsule | 2 Capsules | 0 | 0 |
| 8 pm | 4 Capsules | 1 Capsule | 2 Capsules | 2 Capsules | 1 Capsule |
| | | | DAY 2 | | |
| 8 am | 4 Capsules | 1 Capsule | 2 Capsules | 1 Capsule | 1 Capsule |
| 1 pm | 4 Capsules | 1 Capsule | 2 Capsules | 0 | 0 |
| 8 pm | 4 Capsules | 1 Capsule | 2 Capsules | 2 Capsules | 2 Capsules |

TABLE 1-continued

| DAY 3 TO 14 | | | | | |
|---|---|---|---|---|---|
| Times | Amoxicillin 375 mg | Vonoprazan 20 mg | Bismuth 300 mg | Levofloxacin 375 mg | Rifabutin 120 mg |
| 8 am | 4 Capsules | 1 Capsule | 2 Capsules | 1 Capsule | 1 Capsule |
| 1 pm | 4 Capsules | 1 Capsule | 2 Capsules | 0 | 0 |
| 8 pm | 4 Capsules | 1 Capsule | 2 Capsules | 2 Capsules | 1 Capsule |

H.

| Times | Amoxicillin 375 mg | Vonoprazan 20 mg | Furazolidone 100 mg | Bismuth 300 mg | Rifabutin 60 mg | Levofloxacin 375 mg |
|---|---|---|---|---|---|---|
| DAY 1 | | | | | | |
| 8 am | 4 Capsules | 1 Capsule | 1 Capsule | 2 Capsules | 1 Capsule | 1 Capsule |
| 1 pm | 4 Capsules | 1 Capsule | 1 Capsule | 2 Capsules | 0 | 0 |
| 8 pm | 4 Capsules | 1 Capsule | 1 Capsule | 2 Capsules | 1 Capsule | 2 Capsules |
| DAY 2 | | | | | | |
| 8 am | 4 Capsules | 1 Capsule | 1 Capsule | 2 Capsules | 1 Capsule | 1 Capsule |
| 1 pm | 4 Capsules | 1 Capsule | 1 Capsule | 2 Capsules | 0 | 0 |
| 8 pm | 4 Capsules | 1 Capsule | 1 Capsule | 2 Capsules | 2 Capsules | 2 Capsules |

| DAY 3 TO 14 | | | | | | |
|---|---|---|---|---|---|---|
| Times | Amoxicillin 375 mg | Vonoprazan 20 mg | Furazolidone 100 mg | Bismuth 300 mg | Rifabutin 120 mg | Levofloxacin 375 mg |
| 8 am | 4 Capsules | 1 Capsule | 1 Capsule | 2 Capsules | 1 Capsule | 1 Capsule |
| 1 pm | 4 Capsules | 1 Capsule | 1 Capsule | 2 Capsules | 0 | 0 |
| 8 pm | 4 Capsules | 1 Capsule | 1 Capsule | 2 Capsules | 1 Capsule | 2 Capsules |

I.

| Times | Amoxicillin 375 mg | Vonoprazan 20 mg | Bismuth 300 mg | Tetracycline 250 mg | Rifabutin 60 mg |
|---|---|---|---|---|---|
| DAY 1 | | | | | |
| 8 am | 4 Capsules | 1 Capsule | 2 Capsules | 1 Capsule | 1 Capsule |
| 1 pm | 4 Capsules | 1 Capsule | 2 Capsules | 1 Capsule | 0 |
| 8 pm | 4 Capsules | 1 Capsule | 2 Capsules | 1 Capsule | 1 Capsule |
| DAY 2 | | | | | |
| 8 am | 4 Capsules | 1 Capsule | 2 Capsules | 1 Capsule | 1 Capsule |
| 1 pm | 4 Capsules | 1 Capsule | 2 Capsules | 1 Capsule | 0 |
| 8 pm | 4 Capsules | 1 Capsule | 2 Capsules | 1 Capsule | 2 Capsules |

| DAY 3 TO 14 | | | | | |
|---|---|---|---|---|---|
| Times | Amoxicillin 375 mg | Vonoprazan 20 mg | Bismuth 300 mg | Tetracycline 250 mg | Rifabutin 120 mg |
| 8 am | 4 Capsules | 1 Capsule | 2 Capsules | 1 Capsule | 1 Capsule |
| 1 pm | 4 Capsules | 1 Capsule | 2 Capsules | 1 Capsule | 0 |
| 8 pm | 4 Capsules | 1 Capsule | 2 Capsules | 1 Capsule | 1 Capsule |

J.

| Times | Metronidazole 200 mg | Vonoprazan 20 mg | Bismuth 300 mg | Tetracycline 250 mg | Rifabutin 60 mg |
|---|---|---|---|---|---|
| DAY 1 | | | | | |
| 8 am | 1 Capsule | 1 Capsule | 2 Capsules | 1 Capsule | 1 Capsule |
| 1 pm | 1 Capsule | 1 Capsule | 2 Capsules | 1 Capsule | 0 |
| 8 pm | 1 Capsule | 1 Capsule | 2 Capsules | 1 Capsule | 1 Capsule |
| DAY 2 | | | | | |
| 8 am | 1 Capsule | 1 Capsule | 2 Capsules | 1 Capsule | 1 Capsule |
| 1 pm | 1 Capsule | 1 Capsule | 2 Capsules | 1 Capsule | 0 |
| 8 pm | 1 Capsule | 1 Capsule | 2 Capsules | 1 Capsule | 2 Capsules |

TABLE 1-continued

DAY 3 TO 14

| Times | Metronidazole 200 mg | Vonoprazan 20 mg | Bismuth 300 mg | Tetracycline 250 mg | Rifabutin 120 mg |
|---|---|---|---|---|---|
| 8 am | 1 Capsule | 1 Capsule | 2 Capsules | 1 Capsule | 1 Capsule |
| 1 pm | 1 Capsule | 1 Capsule | 2 Capsules | 1 Capsule | 0 |
| 8 pm | 1 Capsule | 1 Capsule | 2 Capsules | 1 Capsule | 1 Capsule |

K.

| Times | Vonoprazan 20 mg | Bismuth 300 mg | Levofloxacin 375 mg | Rifabutin 60 mg |
|---|---|---|---|---|
| 8 am | 1 Capsule | 2 Capsules | 1 Capsule | 1 Capsule |
| 1 pm | 1 Capsule | 2 Capsules | 0 | 0 |
| 8 pm | 1 Capsule | 2 Capsules | 2 Capsules | 1 Capsule |

DAY 2

| 8 am | 1 Capsule | 2 Capsules | 1 Capsule | 1 Capsule |
|---|---|---|---|---|
| 1 pm | 1 Capsule | 2 Capsules | 0 | 0 |
| 8 pm | 1 Capsule | 2 Capsules | 2 Capsules | 2 Capsules |

DAY 3 TO 14

| Times | Vonoprazan 20 mg | Bismuth 300 mg | Levofloxacin 375 mg | Rifabutin 120 mg |
|---|---|---|---|---|
| 8 am | 1 Capsule | 2 Capsules | 1 Capsule | 1 Capsule |
| 1 pm | 1 Capsule | 2 Capsules | 0 | 0 |
| 8 pm | 1 Capsule | 2 Capsules | 2 Capsules | 1 Capsule |

L.

| Times | Amoxicillin 375 mg | Vonoprazan 20 mg | Furazolidone 100 mg | Rifabutin 60 mg | Bismuth 300 mg | Nitazoxanide 500 mg |
|---|---|---|---|---|---|---|
| 8 am | 4 Capsules | 1 Capsule | 1 Capsule | 1 Capsule | 2 Capsules | 1 Capsule |
| 1 pm | 4 Capsules | 1 Capsule | 1 Capsule | 0 | 2 Capsules | 0 |
| 8 pm | 4 Capsules | 1 Capsule | 1 Capsule | 1 Capsule | 2 Capsules | 1 Capsule |

DAY 2

| 8 am | 4 Capsules | 1 Capsule | 1 Capsule | 1 Capsule | 2 Capsules | 1 Capsule |
|---|---|---|---|---|---|---|
| 1 pm | 4 Capsules | 1 Capsule | 1 Capsule | 0 | 2 Capsules | 0 |
| 8 pm | 4 Capsules | 1 Capsule | 1 Capsule | 2 Capsules | 2 Capsules | 1 Capsule |

DAY 3 TO DAY 14

| Times | Amoxicillin 375 mg | Vonoprazan 20 mg | Furazolidone 100 mg | Rifabutin 120 mg | Bismuth 300 mg | Nitazoxanide 500 mg |
|---|---|---|---|---|---|---|
| 8 am | 4 Capsules | 1 Capsule | 1 Capsule | 1 Capsule | 2 Capsules | 1 Capsule |
| 1 pm | 4 Capsules | 1 Capsule | 1 Capsule | 0 | 2 Capsules | 0 |
| 8 pm | 4 Capsules | 1 Capsule | 1 Capsule | 1 Capsule | 2 Capsules | 1 Capsule |

In alternative embodiments, therapeutic combination as provided herein, and as used to practice methods as provided herein, are formulated and dosaged for oral administration as a powder, e.g., a lyophilised powder, which can be inserted into carriers, e.g., capsules, tablets, geltabs, and the like, e.g., for administration to adults, infants or children to ingest.

In alternative embodiments, therapeutic combination as provided herein, and as used to practice methods as provided herein, are formulated and dosaged for individuals at an age of 2.5 years or above, where the children are unlikely to be able to swallow a capsule; thus, this provided are additional delivery vehicles, products of manufacture and devices to be combined with formulations as provided herein, e.g., powders such as lyophilised powders, e.g., lyophilised powder in a storage vehicle, e.g., capsules, geltabs and the like; for example, provided are delivery vehicles, products of manufacture and devices manufactured as a container, a kit, a package or a pack of a "device and capsule" together, e.g., operably associated such that the container, kit, package or a pack permits individuals, e.g., the very young children and the older children (and including disabled or handicapped individuals) to ingest the product, e.g., the lyophilised product, from the storage vehicle, e.g., capsules, geltabs and the like.

In alternative embodiments, the container, kit, a package or a pack provides the ability of any age child (or disabled or handicapped individual, or any individual) to ingest or swallow the product (e.g., a therapeutic combination, a formulation, pharmaceutical preparation or pharmaceutical composition as provided herein) within the storage vehicle (e.g., capsule) by "draining", e.g., by puncturing, crushing, twisting or turning the container by hand or a device, or otherwise opening, the storage vehicle using a puncturing, crushing or equivalent device (operably built into the container, kit, package or pack), or by hand motion, e.g., by twisting or hand turning (e.g., by hand) the container, and thus allowing passage or contact of the contents of the storage vehicle to enter or pass into an ingestible liquid or other edible substance (e.g., an ice cream or a yoghurt), which is also contained within the container, kit, package or pack, which can be initially (before the twisting or turning, puncturing, crushing or otherwise opening) in a separate compartment from the storage compartment. This twisting or turning, or puncturing, crushing or otherwise opening of the storage compartment and the passage or contact of the contents of the storage vehicle to the ingestible liquid effectively places the contents of the storage (e.g., a powder or freeze-dry comprised of or within a formulation, pharmaceutical preparation or pharmaceutical composition as provided herein) into the ingestible liquid or substance, which can be e.g., water, a milk, a yoghurt, an ice cream, a yogurt, a juice (e.g., a fruit juice, an apple juice), an apple sauce, or a masking drink. The container, kit, package or pack can be designed as an infant feeding bottle, e.g., comprising a nipple or teat for the very young.

In alternative embodiments, this simple twisting or turning, or puncturing or crushing device, allows the storage containers, e.g., geltabs or capsules, to be punctured and/or crushed or otherwise "opened", allowing the contents of the storage container, (e.g., a powder or freeze-dry comprised of or within a therapeutic combination, a formulation, pharmaceutical preparation or pharmaceutical composition as provided herein), to fall out in to the liquid or food compartment, e.g., to the bottom end of a device or straight into a bottle or a container held underneath or configured to be attached and underneath. For example, in this way a provider, e.g., the mother, can purchase a supply of storage containers, e.g., geltabs or capsules, convert them as needed into a powder capable of being mixed a liquid of her choice that the child will be ingesting.

In alternative embodiments, for those capable of swallowing tablets, capsules and the like, the storage containers, e.g., geltabs, tablets or capsules, are manufactured as enteric coated to bypass the acid of the stomach and bile of the duodenum, such that the storage containers, e.g., geltabs, tablets or capsules open (e.g., dissolve) in the jejunum or below.

In alternative embodiments, further provided are instructions for use, e.g., that when emptied into a drink, providers (e.g., the mothers of infants or children) are advised to choose a drink or food that has its own buffering capacity such as flavoured milk, chocolate milk, ice cream, yoghurt, ice blocks, frozen icicles, or simply milk, e.g., that is being fed to the infant or child by a bottle, e.g., a milk bottle, with a nipple or teat.

In alternative embodiments, storage containers, e.g., geltabs, tablets or capsules, or any formulation as provided herein, also comprises an antacid, e.g., a calcium carbonate, magnesium hydroxide, propylene glycol alginate and sodium alginate, or the combination of aluminium hydroxide with magnesium tri silicate, magnesium oxide or magnesium carbonate, so that when the storage container is punctured, crushed or otherwise opened and put into contact with the liquid, e.g., the feeding bottle, and ingested, there will be greater protection from acid damage. In alternative embodiments, methods and instructions further comprise the infant or child also being given an acid suppressant beforehand to permit more viable living bacteria to arrive in the colon.

In alternative embodiments, therapeutic combinations, formulations, pharmaceuticals or pharmaceutical preparations as provided herein are formulated or manufactured as storage vehicles, e.g., tablets, geltabs, pills, capsules and the like; and in alternative embodiments, these storage vehicles are contained in, or contained in a kit with, or packaged with, or sold together with, a storage vehicle 'cracking', puncturing, or otherwise opening or releasing device (e.g., as a powder, e.g., as lyophilised material). These can be dispensed together, or configured together, or manufactured together, as a simple way of meeting the needs of both infants, the very young, older children and needful (e.g., handicapped) adults; e.g., as a powder, e.g., as lyophilised material, e.g., from their storage vehicles, e.g., as encapsulated therapeutic combinations, formulations, pharmaceuticals or pharmaceutical preparations, thus permitting successful clinical administration on a frequent, e.g., bid, tid, or daily, basis for prolonged periods.

Methods of Use and Applications of Devices and Therapeutic Combinations

Multicomponent Packaging

Provided are multi-component delivery systems, e.g., products of manufacture, comprising e.g., formulations, pharmaceutical preparations or pharmaceutical compositions used to practice methods as provided herein, e.g., formulated and dosaged for oral administration as a powder, e.g., a lyophilised powder, and another component, e.g., a liquid; these multi-component delivery systems, e.g., products of manufacture, can be designed or manufactured as described e.g., in U.S. Pat. Nos. 8,968,717; 8,931,665; 7,861,854; 7,018,089; 6,626,912; and, U.S. Pat. App. Pub nos. 2010/0034574; 2009/0180923; 20090232886; 2008/0160076; 2007/0087048; 2007/0036830; 2007/0074979; 2005/0205438; 2004/0089563.

Packaging

Provided are compositions, including preparations, formulations and/or kits, comprising combinations of ingredients, e.g., therapeutic combinations as described herein. In alternative embodiments, therapeutic combination can be mixed and administered together, or alternatively, they can be an individual member of a packaged combination of ingredients, e.g., a liquid component and a solid product component manufactured in a separate compartment, package, kit or container; e.g., where all or a subset of the combinations of ingredients are manufactured in a separate compartment, package or container. In alternative aspects, the package, kit or container comprises a blister package, a clamshell, a tray, a shrink wrap and the like.

In one aspect, the package, kit or container comprises a "blister package" (also called a blister pack, or bubble pack). In one aspect, the blister package is made up of two separate elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, provided are for blister packs, clamshells or trays comprising a formulations, pharmaceutical preparations or pharmaceutical compositions used to practice methods as provided herein. Blister packs, clamshells or trays can be designed to be non-reclosable, so consumers can tell if a package has already opened. They are used to package for sale goods where product tampering is a consideration, such as the pharmaceuticals as provided herein. In one aspect, a blister pack comprises a moulded PVC base, with raised areas (the "blisters") to contain the tablets, pills, etc. comprising the combinations of formulations, pharmaceutical preparations or pharmaceutical compositions as provided herein, covered by a foil laminate. Tablets, pills, etc. are removed from the pack either by peeling the foil back or by pushing the blister to force the tablet to break the foil. In one aspect, a specialized form of a blister pack is a strip pack. In one aspect, in the United Kingdom, blister packs adhere to British Standard 8404.

In one embodiment, provided is a method of packaging wherein the compositions comprising combinations of ingredients are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. are used, and they can comprise of two vacuum-formed PVC sheets meshed together at the edges, with the informative card inside. These can be hard to open by hand, so a pair of scissors or a sharp knife may be required to open.

In one aspect, blister packaging comprises at least two or three or more components: a thermoformed "blister" which houses multi-ingredient combination as provided herein, and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or as large as you would like, but there are limitations and cost considerations in going to an oversized blister card. Conventional blister packs can also be sealed (e.g., using an AERGO 8 DUO™, SCA Consumer Packaging, Inc., DeKalb Ill.) using regular heat seal tooling. This alternative aspect, using heat seal tooling, can seal common types of thermoformed packaging.

In alternative embodiments, therapeutic combinations, formulations, pharmaceutical preparations or pharmaceutical compositions are formulated, e.g., as a powder, e.g., as lyophilised material, e.g., a lyophilized encapsulated product, e.g., for practicing methods as provided herein, can be packaged alone or in combinations, e.g., as "blister packages" or as a plurality of packettes, including as lidded blister packages, lidded blister or blister card or packets or packettes, or a shrink wrap.

In alternative embodiments, laminated aluminium foil blister packs are used, e.g., for the preparation of therapeutic combinations, formulations, pharmaceutical preparations or pharmaceutical compositions as provided herein. Products or kits comprise an aqueous solution(s) which are dispensed (e.g., by measured dose) into containers. Trays can be freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system give tablets an identification mark by embossing a design into the alufoil pocket that is taken up by the tablets when they change from aqueous to solid state. In one aspect, individual 'push-through' blister packs/ packettes are used, e.g., using hard temper aluminium (e.g., alufoil) lidding material. In one aspect, hermetically-sealed high barrier aluminium (e.g., alufoil) laminates are used. In one aspect, products of manufacture include kits or blister packs, use foil laminations and strip packs, stick packs, sachets and pouches, peelable and non-peelable laminations combining foil, paper, or film for high barrier packaging.

Products of Manufacture and Kits

Provided are products of manufacture and kits for practicing methods as provided herein, comprising a therapeutic combination, a formulation, a pharmaceutical preparation or a pharmaceutical composition as provided herein.

In alternative embodiments, multi-component products of manufacture, including kits or blister packs as provided herein, include memory aids to help remind patients when and how to take the therapeutic combination. This safeguards the therapeutic combination's efficacy by protecting each tablet, geltab or pill until it's taken; gives the product or kit portability, makes it easy to take a dose anytime or anywhere.

The invention will be further described with reference to the examples described herein; however, it is to be understood that the invention is not limited to such examples.

A number of embodiments of the invention have been described. Nevertheless, it can be understood that various modifications may be made without departing from the spirit and scope of the invention. Accordingly, other embodiments are within the scope of the following claims.

EXAMPLES

A 47 year old male allergic to penicillin, was referred after five different therapies had failed to eradicate *H. pylori* and he was still symptomatic. To better enhance eradication and dissolve the biofilm the was pre-treated with *Bifidobacterium infantum* three times daily for 4 weeks and this was continued for the next 10 days during the antibiotic treatment. The antibiotic treatment comprised [all ×3 per day] vonoprazan 20 mg; metronidazole 400 mg; bismuth subsalicylate 300 mg; tetracycline HCl 400 mg; and rifabutin 150 mg. When retested by urea breath test 4 weeks after ceasing therapy, the test was negative, showing eradication of the bacteria.

A number of embodiments of the invention have been described. Nevertheless, it can be understood that various modifications may be made without departing from the spirit and scope of the invention. Accordingly, other embodiments are within the scope of the following claims.

What is claimed is:

1. A method for treating, ameliorating, reversing and/or preventing, or acting as a prophylaxis, a *Helicobacter pylori* (*H. pylori*) infection in an individual in need thereof, comprising:
   administering to the individual in need thereof a combination of drugs comprising:
   (a) a composition comprising or consisting of: vonoprazan or a vonoprazan fumarate, or a 5-(2-fluorophenyl)-1-(pyridin-3-ylsulfonyl)-1H-pyrrol-3-yl)-N-methyl-methanamine monofumarate, or a 1-(5-(2-fluorophenyl)-1-(pyridin-3-ylsulfonyl)-1H-pyrrol-3-yl)-N-methyl-methanamine fumarate); and
   (b) an antimicrobial or antibiotic drug or composition comprising:
   (1) an amoxicillin administered to the individual in need thereof at a dose of at least about 250 gm to about 1 g twice daily (bid) or three times daily (tid), or equivalent; and (2) a rifabutin,
wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate) is administered to the individual in need thereof at a dose of: between 50 mg to about 200 mg or more twice daily (bid) or three times daily (tid), or at a unit dosage of at least about 100 mg administered at least once a day, or equivalent.

2. The method of claim 1, wherein the combination of drugs is administered to the individual in need thereof for about 2 or more days.

3. The method of claim 1, wherein the combination of drugs is contained in or comprises a formulation, a pharmaceutical preparation or a pharmaceutical composition.

4. The method of claim 1, wherein the vonoprazan or vonoprazan fumarate, or the 5-(2-fluorophenyl)-1-(pyridin-3-ylsulfonyl)-1H-pyrrol-3-yl)-N-methylmethanamine monofumarate, or the 1-(5-(2-fluorophenyl)-1-(pyridin-3-ylsulfonyl)-1H-pyrrol-3-yl)-N-methyl-methanamine fumarate), is administered to the individual in need thereof in a unit dosage form of between about 40 mg and 200 mgm.

5. The method of claim 1, wherein the combination of drugs, is formulated as a chewable delivery vehicle, a gum, a gummy, a candy, a lozenge, an ice cream or an ice, or a yogurt.

6. The method of claim 1, wherein the combination of drugs further comprises a flavoring or a sweetening agent, an aspartamine, a stevia, monk fruit, a sucralose, a saccharin, a cyclamate, a xylitol, a vanilla, an artificial vanilla or chocolate or strawberry flavor, an artificial chocolate essence, or a mixture or combination thereof.

7. The method of claim 1, wherein the combination of drugs further comprises a preservative, a benzoic acid or a potassium sorbate.

8. The method of claim 1, the combination of drugs further comprises, or has added to
at least one probiotic or prebiotic.

9. The method of claim 1, wherein the combination of drugs further comprises, or has added to: at least one congealing agent,
wherein optionally the congealing agent comprises an arrowroot or a plant starch, a powdered flour, a powdered potato or potato starch, an absorbant polymer, an Absorbable Modified Polymer, and/or a corn flour or a corn starch.

10. The method of claim 1, wherein the combination of drugs further comprises an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient.

11. The method of claim 1, wherein the combination of drugs further comprises, or has added to: at least one Biofilm Disrupting Compound.

12. The method of claim 1, wherein the combination of drugs further comprises, or has added to a statin selected from the group consisting of atorvastatin, fluvastatin, lovastatin, pitavastatin, pravastatin, rosuvastatin, and simvastatin.

13. The method of claim 1, wherein the combination of drugs further comprises or is added to a pronase.

14. The method of claim 1, wherein the combination of drugs is formulated as a delayed or gradual enteric release composition or formulation.

15. The method of claim 1, wherein the combination of drugs is:
(a) contained in a delivery vehicle, product of manufacture, container, syringe, device or bag; or
(b) initially manufactured or formulated as a liquid, a suspension, a gel, a geltab, a semisolid, a tablet, a sachet, a lozenge or a capsule, or as an enteral formulation, or re-formulated for final delivery as a liquid, a suspension, a gel, a geltab, a semisolid, a tablet, a sachet, a lozenge or a capsule, or as an enteral formulation.

16. The method of claim 1, comprising administering to the individual in need thereof a therapeutic combination comprising: amoxicillin, vonoprazan and rifabutin.

17. The method of claim 1, wherein the vonoprazan is administered as a pretreatment to neutralize gastric fluids.

18. The method of claim 1, wherein the amoxicillin is administered to the individual in need thereof at a dose of about 1 g four times daily or equivalent.

19. The method of claim 1, wherein the amoxicillin is formulated as a combination of amoxicillin and clavulanic acid.

20. The method of claim 1, wherein the rifabutin is administered to the individual in need thereof at a dose of between about 50 mg to about 250 mg twice daily (bid) or three times daily (tid).

21. The method of claim 1, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), is administered to the individual in need thereof at a dose of at least about 200 mg a day.

22. The method of claim 21, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), is administered to the individual in need thereof at a dose of at least about 200 mg twice daily (bid).

23. The method of claim 1, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), is administered to the individual in need thereof at a dose of at least about 200 mg three times or more daily (tid) daily.

24. The method of claim 11, wherein the biofilm-disrupting compound comprises a biofilm-disrupting enzyme; a Quorum-sensing inhibitor, a ribonucleic acid III inhibiting peptide, *Salvadora persica* extracts, Competence-stimulating peptide, Patulin and penicillic acid; peptides—cathelicidin-derived peptides, small lytic peptide, PTP-7, Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, *Delisea* furanones, N-sulfonyl homoserine lactones or any combination thereof.

25. The method of claim 24, wherein the biofilm-disrupting enzyme comprises a deoxyribonuclease (DNase), N-acetylcysteine, an auranofin, an alginate lyase, glycoside hydrolase dispersin B.

26. The method of claim 14, wherein the delayed or gradual enteric release composition or formulation comprises:
   (a) a gastro-resistant coating designed to dissolve at a pH of 7 in the terminal ileum;
   (b) an active ingredient coated with an acrylic based resin or equivalent, or
   (c) an acrylic based resin comprising a poly(meth)acrylate or a methacrylic acid copolymer B, NF which dissolves at pH 7 or greater, or
   (d) a multimatrix (MMX) formulation.

27. The method of claim 8, wherein:
   (a) the prebiotic comprises an inulin, lactulose, extracts of artichoke, chicory root, oats, barley, various legumes, garlic, kale, beans or flax or an herb,
   (b) the probiotic comprises a cultured or stool-extracted microorganism or bacteria, or a bacterial component, or
   (c) the bacteria or bacterial component of (b) comprises or is derived from a *Saccharomyces boulardii*, *Bacteroidetes*, a *Firmicutes*, a *Lactobacilli*, a *Bifidobacteria*, an *E coli*, a *Strep fecalis* and equivalents.

28. The method of claim 21, wherein the vonoprazan or a vonoprazan fumarate, or a 5-(2-fluorophenyl)-1-(pyridin-3-ylsulfonyl)-1H-pyrrol-3-yl)-N-methylmethanamine monofumarate, or a 1-(5-(2-fluorophenyl)-1-(pyridin-3-ylsulfonyl)-1H-pyrrol-3-yl)-N-methyl-methanamine fumarate), is administered to the individual in need thereof at a unit dose of about 100 mg,
   optionally administered once a day, bid, tid, or a four times a day, five times a day or six times a day or more a day.

* * * * *